United States Patent [19]
Todo et al.

[11] Patent Number: 6,025,370
[45] Date of Patent: Feb. 15, 2000

[54] QUINOLONECARBOXYLIC ACID DERIVATIVES OR SALTS THEREOF

[75] Inventors: Yozo Todo, Toyama; Kazuya Hayashi, Uozu; Masahiro Takahata, Imizu-gun; Yasuo Watanabe; Hirokazu Narita, both of Toyama, all of Japan

[73] Assignee: Toyama Chemical Co., Ltd., Tokyo, Japan

[21] Appl. No.: 09/125,016

[22] PCT Filed: Feb. 7, 1997

[86] PCT No.: PCT/JP97/00317

§ 371 Date: Aug. 10, 1998

§ 102(e) Date: Aug. 10, 1998

[87] PCT Pub. No.: WO97/29102

PCT Pub. Date: Aug. 14, 1997

[30] Foreign Application Priority Data

Feb. 9, 1996 [JP] Japan ..................................... 8-047936

[51] Int. Cl.[7] .................... A61K 31/475; C07D 215/233; C07D 209/30
[52] U.S. Cl. ........................... 514/312; 546/156; 548/405
[58] Field of Search ........................... 514/312; 546/156; 548/405

[56] References Cited

PUBLICATIONS

Chemical Abstracts 125:86618, abstract of Todo, 1995.

*Primary Examiner*—D. Margaret Seaman
*Attorney, Agent, or Firm*—Oblon, Spivak, McClelland, Maier & Neustadt, P.C.

[57] ABSTRACT

The present invention relates to a quinolone-carboxylic acid derivative represented by the general formula [1], or its salt:

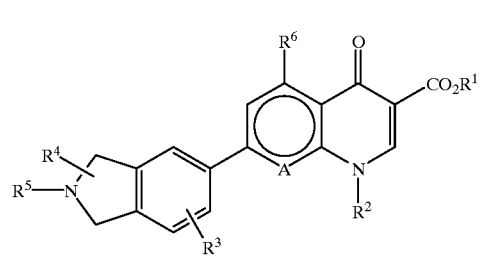

Of the compounds of the present invention, preferable are compounds in which $R^2$ represents a substituted or unsubstituted cycloalkyl group; $R^3$ represents at least one member selected from the group consisting of a hydrogen atom, a halogen atom, a substituted or unsubstituted lower alkyl or lower alkoxy group, and a protected or unprotected hydroxyl or amino group; $R^4$ represents a hydrogen atom or a substituted or unsubstituted lower alkyl group; each of $R^5$ and $R^6$ represents a hydrogen atom; and A represents C—Y in which Y represents a halogen atom, a lower alkyl or lower alkoxy group which may be substituted by one or more halogen atoms, or a protected or unprotected hydroxyl group.

21 Claims, No Drawings

QUINOLONECARBOXYLIC ACID DERIVATIVES OR SALTS THEREOF

This application is a 371 of PCT/JP97/00317, filed Feb. 7, 1997.

TECHNICAL FIELD

This invention relates to a quinolone-carboxylic acid derivative represented by the general formula [1] or its salt:

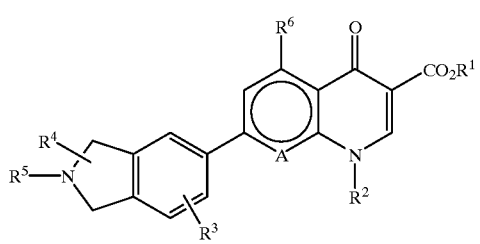

[1]

wherein $R^1$ represents a hydrogen atom or a carboxyl-protecting group; $R^2$ represents a substituted or unsubstituted alkyl, alkenyl, cycloalkyl, aryl or heterocyclic group; $R^3$ represents at least one member selected from the group consisting of a hydrogen atom, a halogen atom, a substituted or unsubstituted alkyl, alkenyl, cycloalkyl, aryl, alkoxy or alkylthio group, a nitro group, a cyano group, an acyl group, a protected or unprotected hydroxyl group, and a protected or unprotected, or substituted or unsubstituted amino group; $R^4$ represents at least one member selected from the group consisting of a hydrogen atom, a halogen atom, a substituted or unsubstituted alkyl, alkenyl, cycloalkyl, aralkyl, aryl, alkoxy or alkylthio group, a protected or unprotected hydroxyl or imino group, a protected or unprotected, or substituted or unsubstituted amino group, an alkylidene group, an oxo group and a group forming a cycloalkane ring together with the carbon atom to which $R^4$ is bonded; $R^5$ represents a hydrogen atom or a substituted or unsubstituted alkyl, cycloalkyl, alkylsulfonyl, arylsulfonyl, acyl or aryl group; $R^6$ represents a hydrogen atom, a halogen atom, a alkysubstituted or unsubstituted alkyl, alkoxy or alkylthio group, a protected or unprotected hydroxyl or amino group, or a nitro group; and A represents CH or C-Y in which Y represents a halogen atom, a substituted or unsubstituted alkyl, alkoxy or alkylthio group, or a protected or unprotected hydroxyl group, the quinolone-carboxylic acid derivative or its salt exhibiting a strong antibacterial activity against Gram-positive bacteria and Gram-negative bacteria, particularly against MRSA.

BACKGROUND ART

Compounds having a quinolonecarboxylic acid skeleton are used as a quinolone type synthetic anti-bacterial agent for curing infectious diseases, but no compound having a carbon-carbon bond between the carbon atom of an isoindoline ring and the carbon atom at the 7-position of a quinolonecarboxylic acid skeleton has been reported at all.

Norfloxacin, Ciprofloxacin, Ofloxacin and the like which have been widely used in clinic as a quinolone type synthetic antibacterial agent are not sufficient in activity against Gram-positive bacteria, in particular, MRSA. Accordingly, there is desired the development of synthetic antibacterial agents which are effective also against these bacteria and have a broad antibacterial spectrum.

DISCLOSURE OF THE INVENTION

Under such circumstances, the present inventors earnestly investigated and consequently found that the compound of the general formula [1] or its salt having a carbon-carbon bond between the carbon atom of an isoindoline ring and the carbon atom at the 7-position of a quinolonecarboxylic acid skeleton exhibits a strong antibacterial activity and is a very safe compound, whereby the present invention has been accomplished. The compound of the present invention is described below in detail.

In the present specification, unless otherwise specified, the term "halogen atom" means a fluorine atom, a chlorine atom, a bromine atom or an iodine atom; the term "alkyl group" means a straight chain or branched chain $C_{1-10}$alkyl group such as methyl, ethyl, n-propyl, isopropyl, n-butyl, isobutyl, sec-butyl, tert-butyl, pentyl, hexyl, heptyl, octyl or the like; the term "lower alkyl group" means a straight chain or branched chain $C_{1-5}$alkyl group such as methyl, ethyl, n-propyl, isopropyl, n-butyl, isobutyl, sec-butyl, tert-butyl, pentyl or the like; the term "alkenyl group" means a straight chain or branched chain $C_{1-10}$alkenyl group such as vinyl, allyl, isopropenyl, butenyl, pentenyl, hexenyl, heptenyl, octenyl or the like; the term "lower alkenyl group" means a straight chain or branched chain $C_{2-5}$alkenyl group such as vinyl, allyl or the like; the term "alkylidene group" means a straight chain or branched chain $C_{1-10}$alkylidene group such as methylene, ethylidene, propylidene, isopropylidene, butylidene, hexylidene, octylidene or the like; the term "lower alkylidene group" means a straight chain or branched chain $C_{1-5}$alkylidene group such as methylene, ethylidene, propylidene, isopropylidene or the like; the term "cycloalkyl group" means a $C_{3-6}$cycloalkyl group such as cyclopropyl, cyclobutyl, cyclopentyl, cyclohexyl or the like; the term "cycloalkane ring" means a $C_{3-6}$cycloalkane ring such as cyclopropane, cyclobutane, cyclopentane, cyclohexane or the like; the term "alkoxy group" means a straight chain or branched chain $C_{1-10}$alkoxy group such as methoxy, ethoxy, n-propoxy, isopropoxy, n-butoxy, isobutoxy, sec-butoxy, tert-butoxy, pentyloxy, hexyloxy, heptyloxy, octyloxy or the like; the term "lower alkoxy group" means a straight chain or branched chain $C_{1-5}$alkoxy group such as methoxy, ethoxy, n-propoxy, isopropoxy, n-butoxy, isobutoxy, sec-butoxy, tert-butoxy, pentyloxy or the like; the term "alkylthio group" means a straight chain or branched chain $C_{1-10}$alkylthio group such as methylthio, ethylthio, n-propylthio, isopropylthio, n-butylthio, isobutylthio, sec-butylthio, tert-butylthio, pentylthio, hexylthio, heptylthio, octylthio or the like; the term "lower alkylthio group" means a straight chain or branched chain $C_{1-5}$alkylthio group such as methylthio, ethylthio, n-propylthio, isopropylthio, n-butylthio, isobutylthio, sec-butylthio, tert-butylthio, pentylthio or the like; the term "alkylsulfonyl group" means a straight chain or branched chain $C_{1-10}$alkylsulfonyl group such as methylsulfonyl, ethylsulfonyl, n-propylsulfonyl, isopropylsulfonyl, n-butylsulfonyl, isobutylsulfonyl, sec-butylsulfonyl, tert-butylsulfonyl, pentylsulfonyl, hexylsulfonyl, heptylsulfonyl, octylsulfonyl or the like; the term "lower alkylsulfonyl group" means a straight chain or branched chain $C_{1-5}$alkylsulfonyl group such as methylsulfonyl, ethylsulfonyl, n-propylsulfonyl, isopropylsulfonyl, n-butylsulfonyl, isobutylsulfonyl, sec-butylsulfonyl, tert-butylsulfonyl, pentylsulfonyl or the like; the term "lower alkylamino group" means an amino group substituted with one or two straight chain or branched chain $C_{1-5}$alkyl groups, such as methylamino, ethylamino, propylamino, butylamino, pentylamino, hexylamino, dimethylamino, diethylamino, methylethylamino, dipropylamino, dibutylamino, dipentylamino or the like; the term "acyl group" means, for example, a formyl group, a straight chain or branched chain $C_{2-5}$alkanoyl group such as acetyl, ethylcarbonyl or the like, or an aroyl group such as benzoyl, naphthylcarbonyl or the like; the term "alkoxycarbonyl group" means an alkoxy —CO— group, in which the prefix "alkoxy" means the above-exemplified straight chain or branched chain $C_{1-10}$ alkoxy group, such as methoxycarbonyl, ethoxycarbonyl, n-propoxycarbonyl, isopropoxycarbonyl, n-butoxycarbonyl, isobutoxycarbonyl, sec-butoxycarbonyl, tert-butoxycarbonyl, pentyloxycarbonyl, hexyloxycarbonyl, heptyloxycarbonyl, octyloxycarbonyl or the like; the term "lower alkoxycarbonyl group" means a lower alkoxy —CO— group, in which the prefix "lower alkoxy" means the above-exemplified straight chain or branched chain $C_{1-5}$ alkoxy group, such as methoxycarbonyl, ethoxycarbonyl, n-propoxycarbonyl, isopropoxycarbonyl, n-butoxycarbonyl, isobutoxycarbonyl, sec-butoxycarbonyl, tert-butoxycarbonyl, pentyloxycarbonyl or the like; the term "aryl group" means, for example, a phenyl or naphthyl group; the term "arylsulfonyl group" means, for example, a phenylsulfonyl or naphthylsulfonyl group; the term "aralkyl group" means, for example, a benzyl or phenethyl group; and the term "heterocyclic group" means a 4-membered, 5-membered or 6-membered cyclic group containing at least one hetero atom selected from the group consisting of oxygen atom, nitrogen atom and sulfur atom as the hetero atom forming the ring or a condensed cyclic group thereof, such as oxetanyl, thietanyl, azetidinyl, furyl, pyrrolyl, thienyl, oxazolyl, isoxazolyl, imidazolyl, thiazolyl, isothiazolyl, pyrrolidinyl, benzofuranyl, benzothiazolyl, pyridyl, quinolyl, pyrimidinyl or morpholinyl group.

The substituent of the lower alkyl, alkyl, lower alkenyl, alkenyl, cycloalkyl, aryl or heterocyclic group for $R^2$; the substituent of the lower alkyl, alkyl, lower alkenyl, alkenyl, cycloalkyl, aryl, lower alkoxy, alkoxy, lower alkylthio, alkylthio or amino group for $R^3$; the substituent of the lower alkyl, alkyl, lower alkenyl, alkenyl, cycloalkyl, aralkyl, aryl, lower alkoxy, alkoxy, lower alkylthio, alkylthio or amino group for $R^4$; the substituent of the lower alkyl, alkyl, cycloalkyl, lower alkylsulfonyl, alkylsulfonyl, arylsulfonyl, acyl or aryl group for $R^5$; the substituent of the lower alkyl, alkyl, lower alkoxy, alkoxy, lower alkylthio or alkylthio group for $R^6$; and the substituent of the lower alkyl, alkyl, lower alkoxy, alkoxy, lower alkylthio or alkylthio group for Y include halogen atoms, cyano group, protected or unprotected carboxyl groups, protected or unprotected hydroxyl groups, protected or unprotected amino groups, protected or unprotected lower alkylamino groups, lower alkyl groups, lower alkoxy groups, lower alkoxycarbonyl groups, aryl groups, cycloalkyl groups, lower alkenyl groups, and lower alkyl groups substituted with one or more halogen atoms. The groups for $R^2$, $R^3$, $R^4$, $R^5$, $R^6$ and Y may be substituted by one or more of the above-exemplified substituents.

The carboxyl-protecting group includes all conventional groups usable as carboxyl-protecting groups, for example, lower alkyl groups such as methyl, ethyl, n-propyl, isopropyl, 1,1-dimethylpropyl, n-butyl, tert-butyl and the like; aryl groups such as phenyl, naphthyl and the like; ar-lower alkyl groups such as benzyl, diphenylmethyl, trityl, p-nitrobenzyl, p-methoxybenzyl, bis(p-methoxyphenyl) methyl and the like; acyl-lower alkyl groups such as acetylmethyl, benzoylmethyl, p-nitrobenzoylmethyl, p-bromobenzoylmethyl, p-methanesulfonylbenzoylmethyl and the like; oxygen-containing heterocyclic groups such as 2-tetrahydro-pyranyl, 2-tetrahydrofuranyl and the like; halogeno-lower alkyl groups such as 2,2,2-trichloroethyl and the like; lower alkylsilylalkyl groups such as 2-(trimethylsilyl)ethyl and the like; acyloxyalkyl groups such as acetoxymethyl, propionyloxymethyl, pivaloyloxymethyl and the like; nitrogen-containing heterocyclic lower alkyl groups such as phthalimidomethyl, succinimidomethyl and the like; cycloalkyl groups such as cyclohexyl and the like; lower alkoxy-lower alkyl groups such as methoxymethyl, methoxyethoxymethyl, 2-(trimethylsilyl) ethoxymethyl and the like; ar-lower alkoxy-lower alkyl groups such as benzyloxymethyl and the like; lower alkylthio-lower alkyl groups such as methylthiomethyl, 2-methylthioethyl and the like; arylthio-lower alkyl groups such as phenylthiomethyl and the like; lower alkenyl groups such as 1,1-dimethyl-2-propenyl, 3-methyl-3-butenyl, allyl and the like; and substituted silyl groups such as trimethylsilyl, triethylsilyl, triisopropylsilyl, diethylisopropylsilyl, tert-butyldimethylsilyl, tert-butyldiphenylsilyl, diphenylmethylsilyl, tert-butylmethoxyphenylsilyl and the like.

The protecting group for each of the amino group, lower alkylamino group and imino group includes all conventional groups usable as amino-protecting groups, for example, acyl groups such as trichloroethoxycarbonyl, tribromoethoxycarbonyl, benzyloxycarbonyl, p-nitrobenzylcarbonyl, o-bromobenzyloxycarbonyl, (mono-, di- or tri-)chloroacetyl, trifluoroacetyl, phenylacetyl, formyl, acetyl, benzoyl, tert-amyloxycarbonyl, tert-butoxycarbonyl, p-methoxybenzyloxycarbonyl, 3,4-dimethoxybenzyloxycarbonyl, 4-(phenylazo) benzyloxycarbonyl, 2-furfuryloxycarbonyl, diphenylmethoxycarbonyl, 1,1-dimethylpropoxycarbonyl, isopropoxycarbonyl, phthaloyl, succinyl, alanyl, leucyl, 1-adamantyloxycarbonyl, 8-quinolyloxycarbonyl and the like; ar-lower alkyl groups such as benzyl, diphenyl-methyl, trityl and the like; arylthio groups such as 2-nitrophenylthio, 2,4-dinitrophenylthio and the like; alkyl- or aryl-sulfonyl groups such as methanesulfonyl, p-toluenesulfonyl and the like; di-lower alkylamino-lower alkylidene groups such as N,N-dimethylaminomethylene and the like; ar-lower alkylidene groups such as benzylidene, 2-hydroxybenzylidene, 2-hydroxy-5-chlorobenzylidene, 2-hydroxy-1-naphthylmethylene and the like; nitrogen-containing heterocyclic alkylidene groups such as 3-hydroxy-4-pyridylmethylene and the like; cycloalkylidene groups such as cyclohexylidene, 2-ethoxycarbonylcyclohexylidene, 2-ethoxycarbonylcyclopentylidene, 2-acetylcyclohexylidene, 3,3-dimethyl-5-oxycyclohexylidene and the like; diaryl- or diar-lower alkylphosphoryl groups such as diphenylphosphoryl, dibenzylphosphoryl and the like; oxygen-containing heterocyclic alkyl groups such as 5-methyl-2-oxo-2H-1,3-dioxol-4-yl-methyl and the like; and substituted silyl groups such as trimethylsilyl and the like.

The protecting group for the hydroxyl group includes all conventional groups usable as hydroxyl-protecting groups, for example, acyl groups such as benzyloxycarbonyl, 4-nitrobenzyloxycarbonyl, 4-bromobenzyloxycarbonyl, 4-methoxybenzyloxycarbonyl, 3,4-dimethoxybenzyloxycarbonyl, methoxycarbonyl, ethoxycarbonyl, tert-butoxycarbonyl, 1,1-dimethylpropoxycarbonyl, isopropoxycarbonyl, isobutyloxycarbonyl, diphenylmethoxycarbonyl, 2,2,2-trichloroethoxycarbonyl, 2,2,2-tribromoethoxycarbonyl, 2-(trimethylsilyl)ethoxycarbonyl, 2-(phenylsulfonyl) ethoxycarbonyl, 2-(triphenylphosphonio)ethoxycarbonyl, 2-furfuryloxycarbonyl, 1-adamantyloxycarbonyl, vinyloxycarbonyl, allyloxycarbonyl, S-benzylthiocarbonyl, 4-ethoxy-1-naphthyloxycarbonyl, 8-quinolyloxycarbonyl, acetyl, formyl, chloroacetyl, dichloroacetyl, trichloroacetyl, trifluoroacetyl, methoxyacetyl, phenoxyacetyl, pivaloyl, benzoyl and the like; lower alkyl groups such as methyl, tert-butyl, 2,2,2-trichloroethyl, 2-trimethylsilylethyl and the like; lower alkenyl groups such as allyl and the like; ar-lower alkyl groups such as benzyl, p-methoxybenzyl, 3,4-dimethoxybenzyl, diphenylmethyl, trityl and the like; oxygen-containing or sulfur-containing hetero-cyclic groups such as tetrahydrofuryl, tetrahydropyranyl, tetrahydrothiopyranyl and the like; lower alkoxy- or lower alkylthio-lower alkyl groups such as methoxymethyl, methylthiomethyl, benzyloxymethyl, 2-methoxyethoxymethyl, 2,2,2-trichloroethoxymethyl, 2-(trimethylsilyl)ethoxymethyl, 1-ethoxyethyl and the like; alkyl- or aryl-sulfonyl groups such as methanesulfonyl, p-toluenesulfonyl and the like; and substituted silyl groups such as trimethylsilyl, triethylsilyl, triisopropylsilyl, diethylisopropylsilyl, tert-butyldimethylsilyl, tert-butyldiphenylsilyl, diphenylmethylsilyl, tert-butylmethoxyphenylsilyl and the like.

The salt of the compound of the general formula [1] includes usually known salts at basic groups such as amino group and the like and salts at acidic groups such as hydroxyl group, carboxyl group and the like. The salts at the basic groups include, for example, salts with mineral acids such as hydrochloric acid, hydrobromic acid, sulfuric acid and the like; salts with organic carboxylic acids such as tartaric acid, formic acid, lactic acid, citric acid, trichloroacetic acid, trifluoroacetic acid and the like; and salts with sulfonic acids such as methanesulfonic acid, benzenesulfonic acid, p-toluenesulfonic acid, mesitylenesulfonic acid, naphthalenesulfonic acid and the like. The salts at the acidic groups include, for example, salts with alkali metals such as sodium, potassium and the like; salts with alkaline earth metals such as calcium, magnesium and the like; ammonium salts; and salts with nitrogen-containing organic bases such as trimethylamine, triethylamine, tributylamine, pyridine, N,N-dimethylaniline, N-methylpiperidine, N-methylmorpholine, diethylamine, dicyclohexylamine, procaine, dibenzylamine, N-benzyl-β-phenethylamine, 1-ephenamine, N,N'-dibenzylethylenediamine and the like. Preferable examples of the salt of the compound of the general formula [1] are pharmaceutically acceptable salts.

Of the compounds according to the present invention, preferable are compounds in which $R^2$ represents a substituted or unsubstituted cycloalkyl group; $R^3$ represents at least one member selected from the group consisting of a hydrogen atom, a halogen atom, a substituted or unsubstituted lower alkyl or lower alkoxy group, and a protected or unprotected hydroxyl or amino group; $R^4$ represents a hydrogen atom or a substituted or unsubstituted lower alkyl group; and each of $R^5$ and $R^6$ represents a hydrogen atom. More preferable are compounds in which $R^2$ represents a cycloalkyl group; $R^3$ represents at least one member selected from the group consisting of a hydrogen atom, a halogen atom, a substituted or unsubstituted lower alkyl group, and a protected or unprotected hydroxyl or amino group; $R^4$ represents a hydrogen atom or a substituted or unsubstituted lower alkyl group; each of $R^5$ and $R^6$ represents a hydrogen atom; and A represents C-Y wherein Y represents a halogen atom, a lower alkyl or lower alkoxy group which may be substituted by one or more halogen atoms, or a protected or unprotected hydroxyl group.

Typical examples of the compound of the present invention are, for example, the following compounds:

1-Cyclopropyl-7-(isoindolin-5-yl)-1,4-dihydro-4-oxoquinoline-3-carboxylic acid,

8-Chloro-1-cyclopropyl-7-(isoindolin-5-yl)-1,4-dihydro-4-oxoquinoline-3-carboxylic acid, 1-Cyclopropyl-8-fluoro-7-(isoindolin-5-yl)-1,4-dihydro-4-oxoquinoline-3-carboxylic acid, 1-Cyclopropyl-7-(isoindolin-5-yl)-8-methyl-1,4-dihydro-4-oxoquinoline-3-carboxylic acid, 1-Cyclopropyl-7-(isoindolin-5-yl)-8-methoxy-1,4-dihydro-4-oxoquinoline-3-carboxylic acid, 1-Cyclopropyl-8-difluoromethoxy-7-(isoindolin-5-yl)-1,4-dihydro-4-oxoquinoline-3-carboxylic acid, 1-Cyclopropyl-7-(isoindolin-5-yl)-8-trifluoromethyl-1,4-dihydro-4-oxoquinoline-3-carboxylic acid, 7-(7-Chloroisoindolin-5-yl)-1-cyclopropyl-8-methyl-1,4-dihydro-4-oxoquinoline-3-carboxylic acid, 1-Cyclopropyl-7-(7-fluoroisoindolin-5-yl)-1,4-dihydro-4-oxoquinoline-3-carboxylic acid, 1-Cyclopropyl-7-(7-fluoroisoindolin-5-yl)-8-methyl-1,4-dihydro-4-oxoquinoline-3-carboxylic acid, 1-Cyclopropyl-7-(7-fluoroisoindolin-5-yl)-8-methoxy-1,4-dihydro-4-oxoquinoline-3-carboxylic acid, 1-Cyclopropyl-8-difluoromethoxy-7-(7-fluoroisoindolin-5-yl)-1,4-dihydro-4-oxoquinoline-3-carboxylic acid, 1-Cyclopropyl-7-(7-fluoroisoindolin-5-yl)-8-trifluoromethyl-1,4-dihydro-4-oxoquinoline-3-carboxylic acid, 1-Cyclopropyl-7-(7-hydroxyisoindolin-5-yl)-8-methoxy-1,4-dihydro-4-oxoquinoline-3-carboxylic acid, 1-Cyclopropyl-8-difluoromethoxy-7-(7-hydroxyisoindolin-5-yl)-1,4-dihydro-4-oxoquinoline-3-carboxylic acid, 7-(7-Aminoisoindolin-5-yl)-1-cyclopropyl-8-methoxy-1,4-dihydro-4-oxoquinoline-3-carboxylic acid, 1-Cyclopropyl-8-methoxy-7-(7-methylisoindolin-5-yl)-1,4-dihydro-4-oxoquinoline-3-carboxylic acid, 1-Cyclopropyl-7-(2-methylisoindolin-5-yl)-1,4-dihydro-4-oxoquinoline-3-carboxylic acid, 1-Cyclopropyl-8-methyl-7-(2-methylisoindolin-5-yl)-1,4-dihydro-4-oxoquinoline-3-carboxylic acid, 1-Cyclopropyl-8-methoxy-7-(2-methylisoindolin-5-yl)-1,4-dihydro-4-oxoquinoline-3-carboxylic acid, 1-Cyclopropyl-8-difluoromethoxy-7-(2-methylisoindolin-5-yl)-1,4-dihydro-4-oxoquinoline-3-carboxylic acid, 1-Cyclopropyl-7-(2-methylisoindolin-5-yl)-8-trifluoromethyl-1,4-dihydro-4-oxoquinoline-3-carboxylic acid, (±)-1-Cyclopropyl-7-(1-methylisoindolin-5-yl)-1,4-dihydro-4-oxoquinoline-3-carboxylic acid, (±)-1-Cyclopropyl-8-methyl-7-(1-methylisoindolin-5-yl)-1,4-dihydro-4-oxoquinoline-3-carboxylic acid, (+)-1-Cyclopropyl-8-methyl-7-(1-methylisoindolin-5-yl)-1,4-dihydro-4-oxoquinoline-3-carboxylic acid, (−)-1-Cyclopropyl-8-methyl-7-(1-methylisoindolin-5-yl)-1,4-dihydro-4-oxoquinoline-3-carboxylic acid, (±)-1-Cyclopropyl-8-methoxy-7-(1-methylisoindolin-5-yl)-1,4-dihydro-4-oxoquinoline-3-carboxylic acid, (+)-1-Cyclopropyl-8-methoxy-7-(1-methylisoindolin-5-yl)-1,4-dihydro-4-oxoquinoline-3-carboxylic acid, (−)-1-Cyclopropyl-8-methoxy-7-(1-methylisoindolin-5-yl)-1,4-dihydro-4-oxoquinoline-3-carboxylic acid, (±)-1-Cyclopropyl-8-difluoromethoxy-7-(1-methylisoindolin-5-yl)-1,4-dihydro-4-oxoquinoline-3-carboxylic acid, (+)-1-Cyclopropyl-8-difluoromethoxy-7-(1-methylisoindolin-5-yl)-1,4-dihydro-4-oxoquinoline-3-carboxylic acid, (−)-1-Cyclopropyl-8-difluoromethoxy-7-(1-methylisoindolin-5-yl)-1,4-dihydro-4-oxoquinoline-3-carboxylic acid, 1-Cyclopropyl-7-(4-fluoroisoindolin-5-yl)-1,4-dihydro-4-oxoquinoline-3-carboxylic acid, 1-Cyclopropyl-7-(4-fluoroisoindolin-5-yl)-8-methyl-1,4-dihydro-4-oxoquinoline-3-carboxylic acid, 1-Cyclopropyl-7-(4-fluoroisoindolin-5-yl)-8-methoxy-1,4-dihydro-4-oxoquinoline-3-carboxylic acid, 1-Cyclopropyl-8-difluoromethoxy-7-(4-fluoroisoindolin-5-yl)-1,4-dihydro-4-oxoquinoline-3-carboxylic acid, 1-Cyclopropyl-7-(4-fluoroisoindolin-5-yl)-8-trifluoromethyl-1,4-dihydro-4-oxoquinoline-3-carboxylic acid, 1-Cyclopropyl-7-(6-fluoroisoindolin-5-yl)-1,4-dihydro-4-oxoquinoline-3-carboxylic acid, 1-Cyclopropyl-7-(6-fluoroisoindolin-5-yl)-8-methyl-1,4-dihydro-4-oxoquinoline-3-carboxylic acid, 1-Cyclopropyl-7-(6-fluoroisoindolin-5-yl)-8-methoxy-1,4-dihydro-4-oxoquinoline-3-carboxylic acid, 1-Cyclopropyl-8-difluoromethoxy-7-(6-fluoroisoindolin-5-yl)-1,4-dihydro-4-oxoquinoline-3-carboxylic acid, 1-Cyclopropyl-7-(6-fluoroisoindolin-5-yl)-8-trifluoromethyl-1,4-dihydro-4-oxoquinoline-3-carboxylic acid, 1-Cyclopropyl-7-(4,7-difluoroisoindolin-5-yl)-1,4-dihydro-4-oxoquinoline-3-carboxylic acid, 1-Cyclopropyl-7-(4,7-difluoroisoindolin-5-yl)-8-methyl-1,4-dihydro-4-oxoquinoline-3-carboxylic acid, 1-Cyclopropyl-7-(4,7-difluoroisoindolin-5-yl)-8-methoxy-1,4-dihydro-4-oxoquinoline-3-carboxylic acid, 1-Cyclopropyl-7-(4,7-difluoroisoindolin-5-yl)-8-difluoromethoxy-1,4-dihydro-4-oxoquinoline-3-carboxylic acid, and 1-Cyclopropyl-7-(4,7-difluoroisoindolin-5-yl)-8-trifluoromethyl-1,4-dihydro-4-oxoquinoline-3-carboxylic acid.

When the compound of the general formula [1] or its salt has isomers (for example, optical isomers, geometrical isomers, tautomers and the like), the present invention includes these isomers, and the compound or its salt may be in the form of a solvate or hydrates or in any of various crystal forms.

Processes for producing the compound of the present invention are explained below.

The compound of the present invention can be synthesized according to, for example, the following production processes.

[Production process 1]

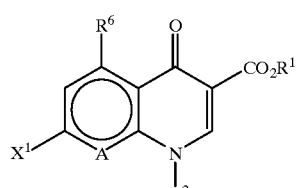

[2] or its salt

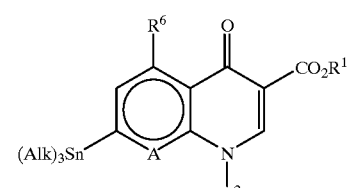

[4] or its salt

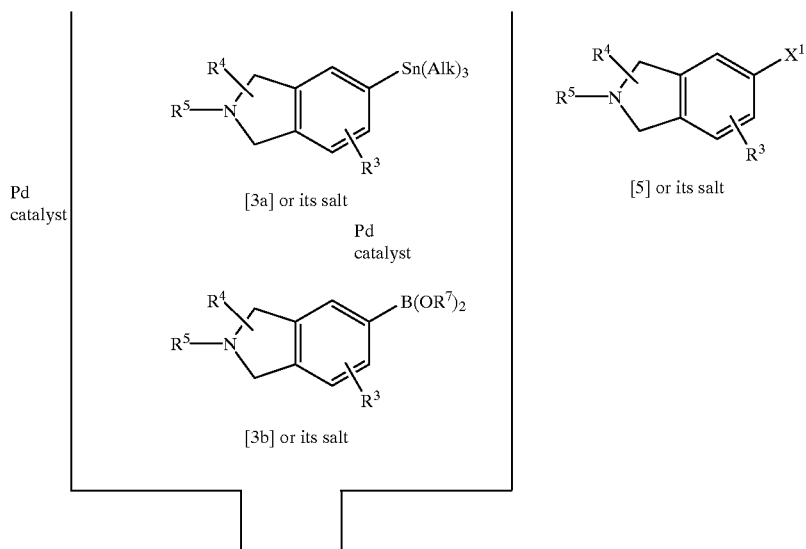

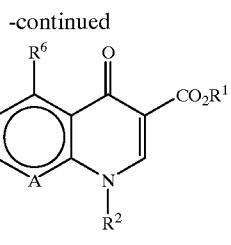

[1] or its salt

[Production process 2]

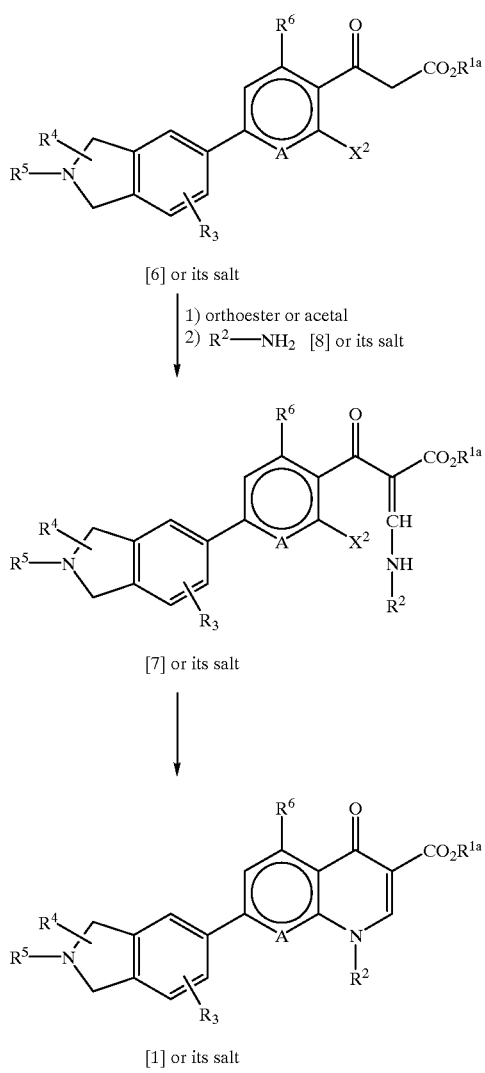

wherein $R^1$, $R^2$, $R^3$, $R^4$, $R^5$, R6 and A are as defined above; $R^7$ represents a hydrogen atom or an alkyl group; $X^1$ represents a chlorine, bromine or iodine atom; Alk represents a straight chain or branched chain alkyl group having 1 to 6 carbon atoms; $X^2$ represents a halogen atom; and $R_{1a}$ represents the same carboxyl-protecting group as for $R^1$.

The salts of the compounds of the general formulas [2], [3a], [3b], [4], [5], [6], [7] and [8] include the same salts as those exemplified as the salt of the compound of the general formula [1].

[Production process 1]

(a) The compound of the general formula [1] or its salt can be obtained by subjecting a combination of a compound of the general formula [2] or its salt and an organotin compound of the general formula [3a] or its salt, or a combination of an organotin compound of the general formula [4] or its salt and a compound of the general formula [5] or its salt to coupling reaction in the presence or absence of silver oxide by using a palladium complex catalyst.

The solvent used in this reaction is not particularly limited so long as it has no undesirable influence on the reaction. The solvent includes, for example, aromatic hydrocarbons such as benzene, toluene, xylene and the like; ethers such as dioxane, tetrahydrofuran, anisole, diethylene glycol diethyl ether, dimethyl Cellosolve and the like; nitriles such as acetonitrile and the like; amides such as N,N-dimethylformamide, N,N-dimethylacetamide and the like; and sulfoxides such as dimethyl sulfoxide and the like. These solvents may be used singly or as a mixture thereof.

The palladium complex catalyst used in the reaction includes, for example, $PdCl_2(PPh_3)_2$, $Pd(PPh_3)_4$, $PdCl_2[P(O\text{-toryl})_3]_2$, $PdCl_2+2P(OEt)_3$ and $PdCl_2(PhCN)_2$, wherein Ph represents a phenyl group and Et represents an ethyl group.

The organotin compound of the general formula [3a] or its salt can be used in an amount of at least 1.0 mole, preferably 1.0 to 2.0 moles, per mole of the compound of the general formula [2] or its salt. The compound of the general formula [5] or its salt can be used in an amount of at least 1.0 mole, preferably 1.0 to 5.0 moles, per mole of the organotin compound of the general formula [4] or its salt.

Usually, the coupling reaction can be carried out at 50–170° C. for 1 minute to 24 hours in an inert gas (e.g., argon or nitrogen) atmosphere.

(b) An alternative process is as follows. The compound of the general formula [1] or its salt can be obtained by subjecting the compound of the general formula [2] or its salt and an organoboron compound of the general formula [3b] or its salt to coupling reaction in the presence or absence of a base by using a palladium complex catalyst.

The solvent used in this reaction is not particularly limited so long as it has no undesirable influence on the reaction. The solvent includes, for example, water; alcohols such as methanol, ethanol, propanol and the like; aromatic hydrocarbons such as benzene, toluene, xylene and the like; halogenated hydrocarbons such as methylene chloride, chloroform, dichloroethane and the like; ethers such as dioxane, tetrahydrofuran, anisole, diethylene glycol diethyl ether, dimethyl Cellosolve and the like; esters such as ethyl acetate, butyl acetate and the like; ketones such as acetone, methyl ethyl ketone and the like; nitriles such as acetonitrile and the like; amides such as N,N-dimethylformamide, N,N-dimethylacetamide and the like; and sulfoxides such as dimethyl sulfoxide and the like. These solvents may be used singly or as a mixture thereof.

The base optionally used in the reaction includes, for example, sodium hydrogencarbonate, sodium carbonate, potassium carbonate and triethylamine. Specific examples of the palladium complex catalyst used in the reaction are the same catalysts as exemplified in section (a) above.

The organoboron compound of the general formula [3b] or its salt can be used in an amount of at least 1.0 mole, preferably 1.0 to 1.5 moles, per mole of the compound of the general formula [2] or its salt.

Usually, the coupling reaction can be carried out at 50–170° C. for 1 minute to 24 hours under an atmosphere of an inert gas (e.g. argon or nitrogen) atmosphere.

[Production process 2]

(1a) A compound of the general formula [7] or its salt can be obtained by reacting a compound of the general formula [6] or its salt with an orthoester such as methyl orthoformate, ethyl orthoformate or the like in acetic anhydride and then with a compound of the general formula [8] or its salt.

The solvent used in these reactions is not particularly limited so long as it has no undesirable influence on the reactions. The solvent includes, for example, aromatic hydrocarbons such as benzene, toluene, xylene and the like; ethers such as dioxane, tetrahydrofuran, anisole, diethylene glycol diethyl ether, dimethyl Cellosolve and the like; alcohols such as methanol, ethanol, propanol and the like; halogenated hydrocarbons such as methylene chloride, chloroform, dichloroethane and the like; amides such as N,N-dimethylformamide, N,N-dimethylacetamide and the like; and sulfoxides such as dimethyl sulfoxide and the like. These solvents may be used singly or as a mixture thereof.

The orthoester can be used in an amount of at least 1 mole, preferably 1 to 10 moles, per mole of the compound of the general formula [6] or its salt.

Usually, the reaction with the orthoester can be carried out at 0–150° C., preferably 50–150° C., for 20 minutes to 50 hours.

In the subsequent reaction with the compound of the general formula [8] or its salt, the compound of the general formula [8] or its salt can be used in an amount of at least 1 mole per mole of the compound of the general formula [6] or its salt. Usually, this reaction can be carried out at 0–100° C., preferably 10–60° C., for 20 minutes to 30 hours.

(1b) An alternative process is as follows. The compound of the general formula [6] or its salt can be converted to the compound of the general formula [7] or its salt by reacting the compound of the general formula [6] or its salt with an acetal such as N,N-dimethylformamide dimethyl acetal, N,N-dimethylformamide diethyl acetal or the like in the presence or absence of an acid anhydride such as acetic anhydride or the like and then with the compound of the general formula [8] or its salt.

The solvent used in these reactions is not particularly limited so long as it has no undesirable influence on the reactions. Specific examples of the solvent are the same solvents as those exemplified in section (1a) above. The acetal can be used in an amount of at least 1 mole, preferably approximately 1–5 moles, per mole of the compound of the general formula [6] or its salt.

Usually, the reaction with the acetal can be carried out at 0–100° C., preferably 20–85° C., for 20 minutes to 50 hours.

In the subsequent reaction with the compound of the general formula [8] or its salt, the compound of the general formula [8] or its salt can be used in an amount of at least 1 mole per mole of the compound of the general formula [6] or its salt. Usually, this reaction can be carried out at 0–100° C., preferably 10–60° C., for 20 minutes to 30 hours.

(2) The compound of the general formula [1] or its salt can be obtained by subjecting the compound of the general formula [7] or its salt to ring-closing reaction in the presence or absence of a fluoride salt or a base.

The solvent used in this reaction is not particularly limited so long as it has no undesirable influence on the reaction. The solvent includes, for example, amides such as N,N-dimethylformamide, N,N-dimethylacetamide and the like; ethers such as dioxane, anisole, diethylene glycol dimethyl ether, dimethyl Cellosolve and the like; and sulfoxides such as dimethyl sulfoxide and the like. These solvents may be used singly or as a mixture thereof.

The fluoride salt optionally used in the reaction includes, for example, sodium fluoride, potassium fluoride and the like. The base optionally used includes, for examples, sodium hydrogencarbonate, potassium carbonate, potassium tert-butoxide, sodium hydride and the like.

The fluoride salt or base can be used in an amount of at least 1.0 mole, preferably 1.0 to 3.0 moles, per mole of the compound of the general formula [7] or its salt.

Usually, the reaction can be carried out at 0–180° C. for 5 minutes to 30 hours.

The thus obtained compound of the general formula [1] or salt thereof can be converted to another compound of the general formula [1] or its salt by subjecting the general formula [1] or salt thereof to one or a proper combination of per se well-known reactions such as oxidation, reduction, rearrangement, substitution, halogenation, dehydration, hydrolysis and the like.

When the compound of the general formula [2], [3a], [3b], [4], [5], [6], [7] or [8] or their salt used in the production processes described above has isomers (for example, optical isomers, geometrical isomers, tautomers and the like), these isomers may be substituted therefor. In addition, the compound or its salt may be used in the form of a solvate or hydrate or in any of various crystal forms.

When the compound of the general formula [2], [3a], [3b], [4], [5], [6], [7], [8] or [1] or their salt has an amino, hydroxyl or carboxyl group, it is possible to previously protect the group with a conventional protecting group and remove the protecting group by a per se well-known method after completion of the reaction.

There are explained below a process for producing the compound of the general formula [2] or its salt or the compound of the general formula [5] or its salt, which is a starting material for producing the compound of the present invention, a process for producing the organotin compound of the general formula [3a] or its salt or the compound of the general formula [4] or its salt, which is a novel compound, and a process for producing the organoboron compound of the general formula [3b] or its salt, which is a novel compound. They can be synthesized according to, for example, the following production processes.

[Production process A]

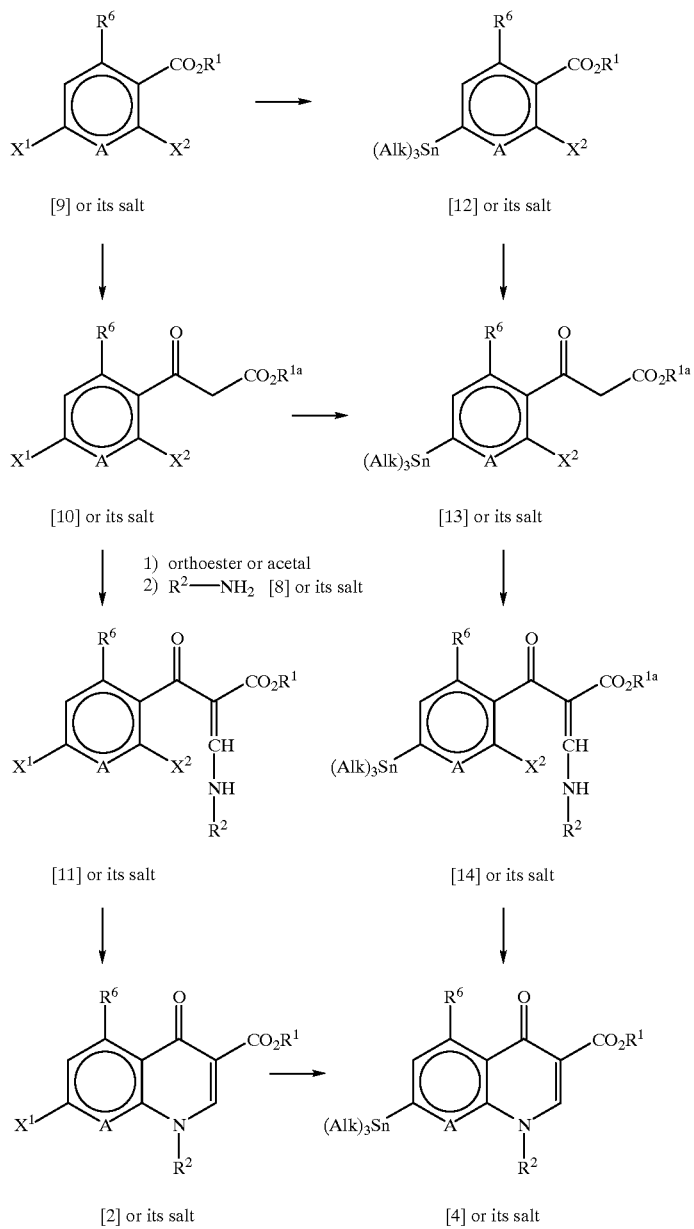
[Production process B]

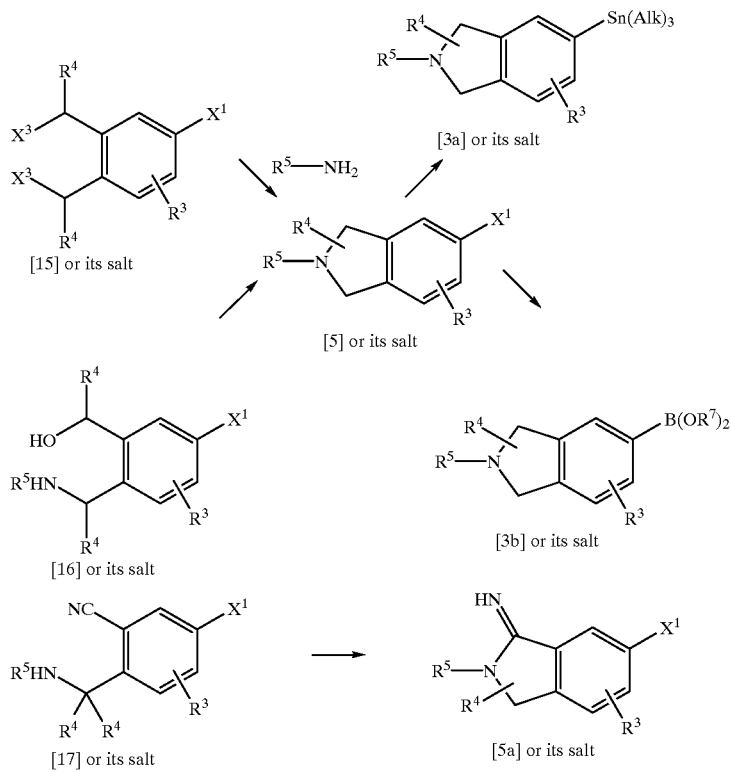
[Production process C]
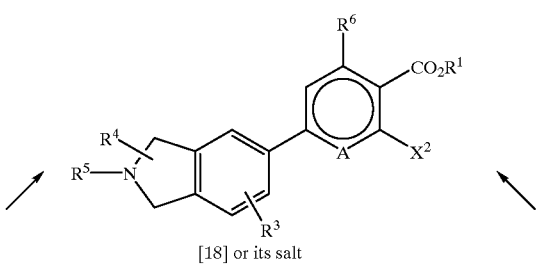

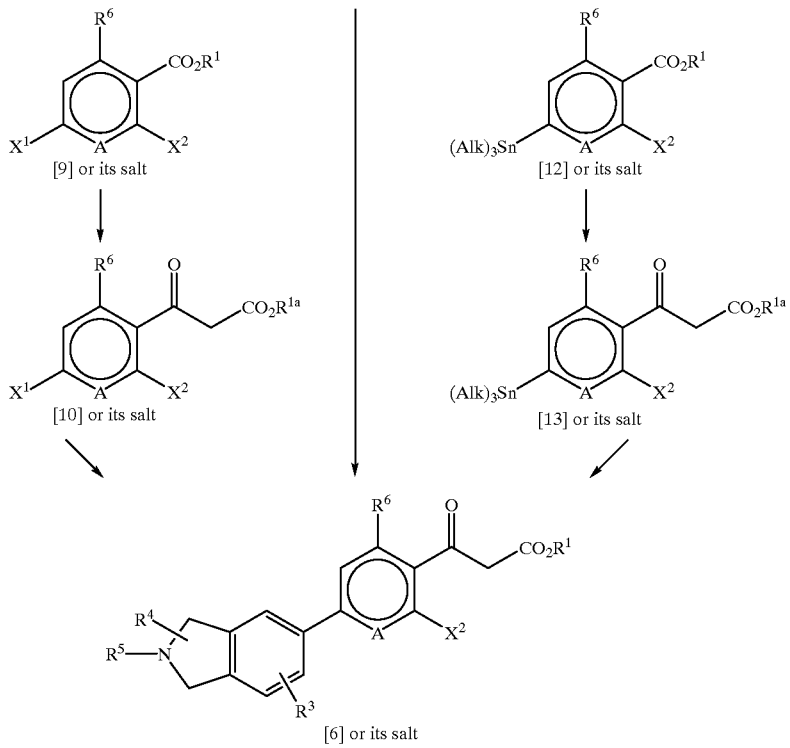

wherein $R^1$, $R^{1a}$, $R^2$, $R^3$, $R^4$, $R^5$, $R^6$, $R^7$, A, $X^1$, $X^2$ and Alk are as defined above, and $X^3$ represents a removing group such as a halogen atom.

The salts of compounds of the general formulas [5a] and [9] to [18] include the same salts as exemplified as the salts of compound of the general formula [1].

Next, production processes A to C are explained below.

(1) Each of a compound of the general formula [9] or its salt and a compound of the general formula [12] or its salt can be obtained, for example, by converting a well-known compound to a compound having a desired atom as X1, by the method disclosed in JP-A-1-100166, namely, the method utilizing the Sandmeyer reaction.

(2) A compound of the general formula [10] or its salt or a compound of the general formula [13] or its salt can be obtained by subjecting the compound of the general formula [9] or its salt or the compound of the general formula [12] or its salt, respectively, to a ketoesterification reaction generally known in the art.

(a) According to the method described in Angewante Chemie International Edition in English, vol. 18, page 72 (1979), the carboxyl group of the compound of the general formula [9] or its salt or the carboxyl group of the compound of the general formula [12] or its salt is reacted with, for example, N,N'-carbonyl diimidazole to convert the compound to an active acid amide, after which the active acid amide is reacted with a magnesium salt of malonic acid monoester, whereby the compound of the general formula [10] or its salt or the compound of the general formula [13] or its salt, respectively, can be obtained.

The solvent used in the reaction of the active acid amide with the magnesium salt of malonic acid monoester is not particularly limited so long as it has no undesirable influence on the reaction. The solvent includes, for example, aromatic hydrocarbons such as benzene, toluene, xylene and the like; ethers such as dioxane, tetrahydrofuran, diethyl ether and the like; halogenated hydrocarbons such as methylene chloride, chloroform, dichloroethane and the like; and amides such as N,N-dimethylformamide, N,N-dimethylacetamide and the like. These solvents may be used singly or as a mixture thereof.

Each of the N,N'-carbonyl diimidazole and the magnesium salt of malonic acid mono-ester can be used in an amount of at least 1 mole, preferably 1 to 2 moles, per mole of the compound of the general formula [9] or [12] or its salt, respectively.

Usually, the reactions can be carried out at 0–100° C., preferably 10–80° C., for 5 minutes to 30 hours.

(b) An alternative process is, for example, as follows. The carboxyl group of the compound of the general formula [9] or its salt or the carboxyl group of the compound of the general formula [12] or its salt is reacted with a halogenating agent such as thionyl chloride to convert the compound to an acid halide, after which the acid halide is reacted with a metal (e.g. sodium or ethoxymagnesium) salt of malonic acid diester, followed by partial removal of the carboxyl-protecting group using p-toluenesulfonic acid in an aqueous solvent or trifluoroacetic acid and decarboxylation, whereby the compound of the general formula [10] or its salt or the compound of the general formula [13] or its salt, respectively, can be obtained.

The solvent used in t he re action of the acid halide with the metal salt of malonic acid diester is not particularly limited so long as it has no undesirable influence on the reaction. Specific examples of the solvent are the same solvents as those exemplified in section (2), sub-section (a) above.

The metal salt of malonic acid diester can be used in an amount of at least 1 mole, preferably 1 to 3 moles, per mole of the compound of the general formula [9] or its salt or the compound of the general formula [12] or its salt.

Usually, the reaction can be carried out at −50° C. to +100° C. for 5 minutes to 30 hours.

(3) (a) A compound of the general formula [11] or its salt or a compound of the general formula [14] or its salt can be obtained by reacting the compound of the general formula [10] or its salt or the compound of the general formula [13] or its salt, respectively, with an orthoester such as methyl orthoformate, ethyl orthoformate or the like in acetic anhydride and then with a compound of the general formula [8] or its salt.

These reactions may be carried out by the same method as described in production process 2, section (1a).

(b) An alternative process is as follows. The compound of the general formula [10] or its salt or the compound of the general formula [13] or its salt may be reacted with an acetal such as N,N-dimethylformamide dimethyl acetal, N,N-dimethylformamide diethyl acetal or the like in the presence or absence of an acid anhydride such as acetic anhydride or the like and then reacted with the compound of the general formula [8] or its salt to be converted to the compound of the general formula [11] or its salt or the compound of the general formula [14] or its salt, respectively.

These reactions may be carried out by the same method as described in production process 2, (1b).

(4) The compound of the general formula [2] or its salt or the compound of the general formula [4] or its salt can be obtained by subjecting the compound of the general formula [11] or its salt or th e compound of the general formula [14] or its salt, respectively, to ring-closing reaction in the presence or absence of a fluoride salt or a base.

The reaction may be carried out by the same method as described in production process 2, section (2).

(5) The aryltin compound of the general formula [12] or its salt, the aryltin compound of the general formula [13] or its salt, or the aryltin compound of the general formula [4] or its salt can be obtained by reacting the halogenated aryl compound of the general formula [9] or its salt, the halogenated aryl compound of the general formula [10] or its salt, or the halogenated aryl compound of the general formula [2] or its salt, respectively, with a hexaalkyldistannane by the use of a palladium complex catalyst according to the method described, for example, in Bulletin of the Chemical Society of Japan vol. 56, pages 3855–3856 (1983).

The solvent and the palladium complex catalyst which are used in this reaction are not particularly limited so long as they have no undesirable influence on the reaction. Specific examples of the solvent and the palladium complex catalyst are the same as those given in the above production process 1.

The hexaalkyldistannane can be used in an amount of at least 1.0 mole, preferably 1.0 to 3.0 moles, per mole of the halogenated aryl compound of the general formula [9], [10] or [2] or their salt.

Usually, the reaction can be carried out at 40–160° C. for 1 to 72 hours.

(6) The compound of the general formula [3a] or its salt can be obtained by reacting the compound of the general formula [5] or its salt with a hexaalkyldistannane by the use of a palladium complex catalyst in the same manner as described in section (5) above.

(7) The compound of the general formula [3b] or its salt can be produced according to the process described in Jikken Kagaku Koza, 4th edition, vol. 24, pages 61–90 (1992). Specifically, the compound of the general formula [3b] or its salt can be obtained by subjecting the compound of the general formula [5] or its salt to lithiation or Grignard reaction and then reacting the reaction product with a trialkyl borate.

(8) The compound of the general formula [5] or its salt can be produced according to, for example, any of the process described in Organic Synthesis, vol. 5, pages 1064–1066 and the processes disclosed in JP-A-63-179872, JP-A-2-62875 and JP-A-3-52888, and the process described in Arzniem.-Forsh./Drug Res. 30(II), 1487–1493 (1980).

Specifically, the compound of the general formula [5] or its salt can be obtained by reacting a compound of the general formula [15] or its salt with $R^5NH_2$ or subjecting a compound of the general formula [16] or its salt to dehydrating reaction.

On the other hand, a compound of the general formula [5a] or its salt, which has an imino group, can be obtained by subjecting a compound of the general formula [17] or its salt to ring-closing reaction.

(9) The compound of the general formula [6] or its salt can be produced from the compound of the general formula [10] or its salt or the compound of the general formula [13] or its salt according to the same process as described in production process 1. It can be obtained also by subjecting a compound of the general formula [18] or its salt to ketoesterification according to the method described above.

The compound of the general formula [10] or its salt or the compound of the general formula [13] or its salt can be obtained by subjecting the compound of the general formula [9] or its salt or the compound of the general formula [12] or its salt, respectively, to ketoesterification according to the method described above.

On the other hand, the compound of the general formula [18] or its salt can be produced from the compound of the general formula [9] or its salt or the compound of the general formula [12] or its salt according to the same process as described in production process 1.

In production processes A to C, when any of the compounds of the general formulas [2] to [18] or their salts has an amino, hydroxyl or carboxyl group, it is possible to protect the group with a conventional protecting group previously and remove the protecting group by a per se well-known method after completion of the reaction.

When any of the compounds of the general formulas [2] to [18] or their salts has isomers (for example, optical isomers, geometrical isomers, tautomers and the like), these isomers may be substituted therefor. In addition, the compounds or their salts may be used in the form of a solvate or hydrate or in any of various crystal forms. Furthermore, after completion of each reaction, the reaction product may be used as it is in the subsequent reaction without isolation.

The thus obtained compound of the general formula [1] or salt thereof can be isolated and purified according to one or more conventional operations which may be selected from extraction, crystallization, column chromatography and the like.

When used as a pharmaceutical, the compound of the present invention may be properly mixed with a preparation adjuvant such as an excipient, a carrier or a diluent which is usually used for formulation into a pharmaceutical form. The compound can be administered orally or parenterally in the form of tablets, capsules, a powder, a syrup, granules, pills, a suspension, an emulsion, a solution, a powdery formulation, a suppository, an ointment, an injection or the like. The administration route, dose and number of administrations may be properly chosen depending on the age, body weight and symptom of a patient. Usually, the compound may be administered to an adult in a dose of 0.1 to 100 mg/kg per day in one portion or several portions orally or parenterally (for example, by injection, drip infusion or intrarectal administration).

Next, the pharmacological activity of typical compounds of the present invention is explained below.

[Test compounds]

a: 1-Cyclopropyl-7-(isoindolin-5-yl)-8-methyl-1,4-dihydro-4-oxoquinoline-3-carboxylic acid, b: 1-Cyclopropyl-7-(7-fluoroisoindolin-5-yl)-8-methyl-1,4-dihydro-4-oxoquinoline-3-carboxylic acid, c: 1-Cyclopropyl-7-(isoindolin-5-yl)-8-methoxy-1,4-dihydro-4-oxoquinoline-3-carboxylic acid, d: 1-Cyclopropyl-7-(7-fluoroisoindolin-5-yl)-8-methoxy-1,4-dihydro-4-oxoquinoline-3-carboxylic acid, e: 1-Cyclopropyl-8-difluoromethoxy-7-(isoindolin-5-yl)-1,4-dihydro-4-oxoquinoline-3-carboxylic acid, f: 1-Cyclopropyl-8-difluoromethoxy-7-(7-fluoroisoindolin-5-yl)-1,4-dihydro-4-oxoquinoline-3-carboxylic acid, g: (±)-1-Cyclopropyl-8-difluoromethoxy-7-(1-methylisoindolin-5-yl)-1,4-dihydro-4-oxoquinoline-3-carboxylic acid, h: (+)-1-Cyclopropyl-8-difluoromethoxy-7-(1-methylisoindolin-5-yl)-1,4-dihydro-4-oxoquinoline-3-carboxylic acid, i: (−)-1-Cyclopropyl-8-difluoromethoxy-7-(1-methylisoindolin-5-yl)-1,4-dihydro-4-oxoquinoline-3-carboxylic acid, and j: 1-Cyclopropyl-6-fluoro-7-(1-piperazinyl)-1,4-dihydro-4-oxoquinoline-3-carboxylic acid (Ciprofloxacin; reference compound).

1. Antibacterial Activity

[Test method]

According to the standard method of Japan Society of Chemotherapy [CHEMOTHERAPY, vol. 29, No. 1, pages 76–79 (1981)], a loopful of a cell suspension obtained by culturing in Mueller Hinton broth (mfd. by Difco) at 37° C. for 20 hours and adjusted to a concentration of $10^6$ cells/plate ($10^8$ cells/ml) was inoculated into a Mueller Hinton agar medium (mfd. by Difco) containing the test compound, followed by incubation at 37° C. for 20 hours. Then, the cell growth was observed to determine the minimum concentration at which the cell growth was inhibited, which concentration is indicated as MIC (μg/ml). Table 1 shows the results obtained. In Table 1, *1 to *4 denote the following strains:

1: *Staphylococcus aureus*

2: β-lactamase-producing *S. aureus*

3: methicillin-resistant *S. aureus*

4: *Escherichia coli*.

sodium hydroxide solution. As a result, it was found that the median lethal dose ($LD_{50}$) values of compounds e, g and i were 200 mg/kg or more.

BEST MODE FOR CARRYING OUT THE INVENTION

The present invention is illustrated with reference to the following reference examples and examples, which should not be construed as limiting the scope of the invention.

In the reference examples and the examples, the mixing ratios in the eluents are all by volume, and Silica gel 60 of 70 to 230 mesh (mfd. by MERCK & CO., INC.) or that of 100 to 270 mesh (mfd. by FUJI SILYSIA CHEMICAL LTD.) was used as a carrier in the column chromatography and LC-SORB SP-A-Si of Chemco Scientific Co., Ltd. was used as a carrier in the intermediate-pressure column chromatography. The symbol used in the reference examples and the examples has the following meaning:

$d_1$-TFA: a trifluoroacetic acid-$d_1$.

$d_6$-DMSO: a dimethylsulfoxide-$d_6$.

REFERENCE EXAMPLE 1

(1) In 254 ml of N,N-dimethylformamide was dissolved 25.4 g of 2,6-difluorophenol, followed by adding thereto 29.7 g of potassium carbonate and 83.1 g of iodomethane, and the resulting mixture was stirred at 50° C. for 2 hours. The reaction mixture was added to a mixed solvent of 200 ml of diethyl ether and 600 ml of water and the organic layer was separated. The organic layer obtained was washed with water and then a saturated aqueous sodium chloride solution, dried over anhydrous magnesium sulfate, and then distilled under reduced pressure to remove the solvent. The resulting residue was purified by vacuum distillation (43–45° C./20 mmHg) to obtain 22.9 g of 2,6-difluoroanisole as a colorless oil.

(2) In 350 ml of tetrahydrofuran was dissolved 22.9 g of 2,6-difluoroanisole, and to the solution was added dropwise 110 ml of a 1.6 M solution of n-butyllithium in n-hexane at −70° C. over a period of 30 minutes. The resulting mixture was stirred at the same temperature for 1 hour, and carbon dioxide was introduced thereinto, after which the mixture was heated to 0° C. over a period of 1 hour. The reaction mixture was added to a mixed solvent of 300 ml of ethyl acetate and 700 ml of water and the pH was adjusted to 1 with 6N hydrochloric acid, after which the organic layer was separated. The organic layer obtained was washed with a saturated aqueous sodium chloride solution, followed by

TABLE 1

| | MIC (μg/ml) | | | | | | | | | |
|---|---|---|---|---|---|---|---|---|---|---|
| | a | b | c | d | e | f | g | h | i | j |
| *S. aureus* FDA209P*1 | ≦0.05 | ≦0.05 | ≦0.05 | ≦0.05 | ≦0.05 | ≦0.05 | ≦0.05 | ≦0.05 | ≦0.05 | 0.2 |
| *S. aureus* F-137*2 | ≦0.05 | ≦0.05 | ≦0.05 | ≦0.05 | ≦0.05 | ≦0.05 | ≦0.05 | ≦0.05 | ≦0.05 | 0.39 |
| *S. aureus* F-597*3 | 0.1 | ≦0.05 | 0.1 | ≦0.05 | 0.1 | ≦0.05 | 0.1 | 0.2 | ≦0.05 | 3.13 |
| *E. coli* NIHJ JC-2*4 | ≦0.05 | ≦0.05 | ≦0.05 | ≦0.05 | ≦0.05 | ≦0.05 | ≦0.05 | ≦0.05 | ≦0.05 | ≦0.05 |

2. Acute Toxicity

Each test compound was intravenously administered to groups of 4 ddy strain mice (body weight: 30±1 g) each, whereby its acute toxicity was investigated. In this case, the compound was administered in the form of a solution prepared by dissolving the compound in a 0.1 N aqueous adding thereto a solution of diazomethane in diethyl ether, and the resulting mixture was stirred at room temperature for 10 minutes and distilled under reduced pressure to remove the solvent. The resulting residue was purified by a column chromatography (eluent; n-hexane:ethyl acetate=10:1) to obtain 16.8 g of methyl 2,4-difluoro-3-methoxybenzoate as colorless crystals.

IR (KBr) cm$^{-1}$: νc=o 1718.

NMR (CDCl$_3$) δ values: 3.92(3H, s), 3.99(3H, s), 6.50–7.10(1H, m), 7.20–7.90(1H, m).

REFERENCE EXAMPLE 2

(1) In 20 ml of methylene chloride was dissolved 2.00 g of methyl 2,4-difluoro-3-methoxy-benzoate, and to the solution was added 12.8 ml of a 1 M solution of boron tribromide in methylene chloride at −30° C., after which the resulting mixture was stirred under ice-cooling for 2 hours. The reaction mixture was added to a mixed solvent of 150 ml of ethyl acetate and 150 ml of water and the organic layer was separated. The organic layer obtained was washed with a saturated aqueous sodium chloride solution, dried over anhydrous magnesium sulfate, and then distilled under reduced pressure to remove the solvent. The resulting residue was purified by a column chromatography (eluent; n-exane:ethyl acetate=3:1) to obtain 1.35 g of methyl 2,4-difluoro-3-hydroxybenzoate as colorless crystals.

(2) In 20 ml of N,N-dimethylformamide was dissolved 1.00 g of methyl 2,4-difluoro-3-hydroxy-benzoate, followed by adding thereto 0.88 g of potassium carbonate and then 12 ml of a 6 M solution of chlorodifluoromethane in N,N-dimethylformamide, and the resulting mixture was stirred in a sealed tube at 120–130° C. for 2.5 hours. The reaction mixture was added to a mixed solvent of 100 ml of ethyl acetate and 200 ml of water and the pH was adjusted to 2 with 6N hydrochloric acid, after which the organic layer was separated. The organic layer obtained was washed with a saturated aqueous sodium chloride solution, dried over anhydrous magnesium sulfate, and then distilled under reduced pressure to remove the solvent. The resulting residue was purified by a column chromatography (eluent; n-hexane:ethyl acetate=4:1) to obtain 1.02 g of methyl 2,4-difluoro-3-difluoromethoxybenzoate as colorless crystals.

IR (KBr) cm$^{-1}$: νc=o 1708.

REFERENCE EXAMPLE 3

(1) In 47 ml of dimethyl sulfoxide was dissolved 4.65 g of ethyl 2,4-difluoro-3-methylbenzoate, followed by adding thereto 3.32 g of sodium azide, and the resulting mixture was stirred at 70° C. for 20 hours. The reaction mixture was cooled to room temperature and then added to a mixed solvent of 150 ml of toluene and 150 ml of water, and the organic layer was separated. The organic layer obtained was washed with water and then a saturated aqueous sodium chloride solution, dried over anhydrous magnesium sulfate, and then distilled under reduced pressure to remove the solvent. The resulting residue was purified by a column chromatography (eluent: toluene) to obtain 2.20 g of ethyl 4-azido-2-fluoro-3-methylbenzoate as a light-yellow oil.

(2) In 40 ml of ethanol was dissolved 2.00 g of ethyl 4-azido-2-fluoro-3-methylbenzoate, followed by adding thereto 0.40 g of 5% palladium-carbon, and the resulting mixture was stirred at room temperature for 5 hours under a hydrogen atmosphere. The reaction mixture was filtered and the filtrate was concentrated under reduced pressure. The resulting residue was purified by a column chromatography (eluent; toluene:ethyl acetate=10:1) to obtain 0.75 g of ethyl 4-amino-2-fluoro-3-methylbenzoate as colorless crystals.

(3) In 7 ml of ethanol was suspended 0.70 g of ethyl 4-amino-2-fluoro-3-methylbenzoate, followed by adding thereto 7 ml of 1N sodium hydroxide, and the resulting mixture was stirred at 40° C. for 4 hours. To the reaction mixture was added 1.2 ml of 6N hydrochloric acid, followed by extraction with 50 ml of ethyl acetate. The extract solution was washed with a saturated aqueous sodium chloride solution, dried over anhydrous magnesium sulfate, and then distilled under reduced pressure to remove the solvent, to obtain 0.59 g of 4-amino-2-fluoro-3-methylbenzoic acid as colorless crystals.

IR (KBr) cm-1: νc=o 1671, 1632.

The following compounds were obtained in the same manner as above.

4-Amino-2,3-difluorobenzoic acid IR (KBr) cm$^{-1}$: νc=o 1685, 1642.

4-Amino-2-fluoro-3-methoxybenzoic acid IR (KBr) cm$^{-1}$: νc=o 1679, 1624.

4-Amino-2-fluoro-3-difluoromethoxybenzoic acid IR (KBr) cm$^{-1}$: νc=o 1686, 1636.

4-Amino-3-chloro-2-fluorobenzoic acid IR (KBr) cm$^{-1}$: νc=o 1684, 1626.

4-Amino-2-fluoro-3-trifluoromethylbenzoic acid IR (KBr) cm$^{-1}$: νc=o 1684, 1636.

REFERENCE EXAMPLE 4

In 14 ml of 4.7% hydrobromic acid was suspended 0.55 g of 4-amino-2-fluoro-3-methylbenzoic acid, and 3.7 g of cupric bromide was added thereto. To the resulting suspension was added dropwise a solution of 0.38 g of sodium nitrite in 4 ml of water under ice-cooling over a period of 15 minutes, and the resulting mixture was stirred at the same temperature for 1 hour and then at room temperature for 24 hours. To the reaction mixture was added 20 ml of toluene and the organic layer was separated. The organic layer obtained was washed with 20 ml of 20% hydrobromic acid, dried over anhydrous magnesium sulfate, and then distilled under reduced pressure to remove the solvent. n-Hexane was added to the resulting residue and the crystals were collected by filtration to obtain 0.68 g of colorless 4-bromo-2-fluoro-3-methylbenzoic acid.

IR (KBr) cm$^{-1}$: νc=o 1690.

The following compounds were obtained in the same manner as above.

4-Bromo-2,3-difluorobenzoic acid IR (KBr) cm$^{-1}$: νc=o 1691.

4-Bromo-2-fluoro-3-methoxybenzoic acid IR (KBr) cm-1: νc=o 1694.

4-Bromo-2-fluoro-3-difluoromethoxybenzoic acid IR (KBr) cm-1: νc=o 1696.

4-Bromo-3-chloro-2-fluorobenzoic acid IR (KBr) cm-1: νc=o 1687.

4-Bromo-2-fluoro-3-trifluoromethylbenzoic acid IR (KBr) cm-1: νc=o 1698.

REFERENCE EXAMPLE 5

In 13 ml of anhydrous tetrahydrofuran was dissolved 0.65 g of 4-bromo-2-fluoro-3-methylbenzoic acid, followed by adding thereto 0.92 g of N,N'-carbonyldiimidazole under ice-cooling, and the resulting mixture was stirred at room temperature for 2 hours. Then, 0.81 g of magnesium ethoxy-carbonylacetate was added thereto and the resulting mixture was stirred at the same temperature for 20 hours. The reaction mixture was added to a mixed solvent of 50 ml of toluene and 50 ml of water and the pH was adjusted to 1 with 6N hydrochloric acid, after which the organic layer was separated. The organic layer obtained was washed successively with a saturated aqueous sodium hydrogen-carbonate solution, water and a saturated aqueous sodium chloride solution, dried over anhydrous magnesium sulfate, and then distilled under reduced pressure to remove the solvent. The resulting residue was purified by a column chromatography (eluent: toluene) to obtain 0.70 g of ethyl 4-bromo-2-fluoro-3-methylbenzoylacetate as colorless crystals.

IR (KBr) cm$^{-1}$: vc=o 1616.

The following compounds were obtained in the same manner as above.

Ethyl 4-bromo-2,3-difluorobenzoylacetate IR (neat) cm$^{-1}$: vc=o 1744, 1697, 1627.

Ethyl 4-bromo-2-fluoro-3-methoxybenzoylacetate IR (neat) cm$^{-1}$: vc=o 1743, 1691, 1624.

Ethyl 4-bromo-2-fluoro-3-difluoromethoxybenzoylacetate IR (neat) cm$^{-1}$: vc=o 1742, 1696, 1624.

Ethyl 4-bromo-3-chloro-2-fluorobenzoylacetate IR (KBr) cm$^{-1}$: vc=o 1723, 1674, 1628.

Ethyl 4-bromo-2-fluoro-3-trifluoromethylbenzoyl-acetate IR (KBr) cm$^{-1}$: vc=o 1744, 1670, 1637.

REFERENCE EXAMPLE 6

(1) In 14 ml of methylene chloride was dissolved 0.70 g of ethyl 4-bromo-2-fluoro-3-methyl-benzoylacetate, followed by adding thereto 0.29 g of acetic anhydride and 0.33 g of N,N-dimethylformamide dimethyl acetal, and the resulting mixture was stirred at room temperature for 2 hours and then distilled under reduced pressure to remove the solvent. The resulting residue was dissolved in 10 ml of ethanol, followed by adding thereto 0.16 g of cyclopropylamine. The resulting mixture was stirred at room temperature for 12 hours and the crystals precipitated were collected by filtration to obtain 0.72 g of colorless ethyl 2-(4-bromo-2-fluoro-3-methylbenzoyl)-3-cyclopropylaminoacrylate.

(2) In 7 ml of dimethyl sulfoxide was dissolved 0.72 g of ethyl 2-(4-bromo-2-fluoro-3-methylbenzoyl)-3-cyclopropylaminoacrylate, followed by adding thereto 0.48 g of potassium carbonate, and the resulting mixture was stirred at 90° C. for 30 minutes. The reaction mixture was cooled to room temperature, after which 35 ml of water was added thereto and the crystals were collected by filtration to obtain 0.66 g of colorless ethyl 7-bromo-1-cyclopropyl-8-methyl-1,4-dihydro-4-oxoquinoline-3-carboxylate.

IR (KBr) cm$^{-1}$: vc=o 1684, 1636.

NMR (CDCl$_3$) δ values: 0.70–1.60(7H, m), 2.85(3H, s), 3.70–4.10(1H, m), 4.38(2H, q, J=7.5 Hz), 7.58(1H, d, J=9.0 Hz), 8.15(1H, d, J=9.0 Hz), 8.63(1H, s).

The following compounds were obtained in the same manner as above.

Ethyl 7-bromo-1-cyclopropyl-8-fluoro-1,4-dihydro-4-oxoquinoline-3-carboxylate
IR (KBr) cm$^{-1}$: vc=o 1684, 1652.
NMR (CDCl$_3$) δ values: 0.90–1.60(7H, m), 3.50–4.00 (1H, m), 4.38(2H, q, J=7.5 Hz), 7.54(1H, dd, J=6.0,9.0 Hz), 8.15(1H, dd, J=1.5,9.0 Hz), 8.55(1H, s).

Ethyl 7-bromo-1-cyclopropyl-8-methoxy-1,4-dihydro-4-oxoquinoline-3-carboxylate
IR (KBr) cm$^{-1}$: vc=o 1694, 1642.
NMR (CDCl$_3$) δ values: 0.60–1.70(7H, m), 3.50–4.10 (4H, m), 4.37(2H, q, J=7.0 Hz), 7.55(1H, d, J=9.0 Hz), 8.12(1H, d, J=9.0 Hz), 8.57(1H, s).

Ethyl 7-bromo-1-cyclopropyl-8-difluoromethoxy-1,4-dihydro-4-oxoquinoline-3-carboxylate
IR (KBr) cm$^{-1}$: vc=o 1687, 1640.
NMR (CDCl$_3$) δ values: 0.70–1.70(7H, m), 3.70–4.70 (3H, m), 6.52(1H, t, J=74.5 Hz), 7.58(1H, d, J=8.5 Hz), 8.24(1H, d, J=8.5 Hz), 8.59(1H, s).

Ethyl 7-bromo-8-chloro-1-cyclopropyl-1,4-dihydro-4-xoquinoline-3-carboxylate
IR (KBr) cm$^{-1}$: vc=o 1697, 1663.
NMR (CDCl$_3$) δ values: 0.80–1.60(7H, m), 4.10–4.60 (3H, m), 7.68 (1H, d, J=8.5 Hz), 8.23(1H, d, J=8.5 Hz), 8.67(1H, s).

Ethyl 7-bromo-1-cyclopropyl-8-trifluoromethyl-1,4-dihydro-4-oxoquinoline-3-carboxylate
IR (KBr) cm$^{-1}$: vc=o 1697, 1659.
NMR (CDCl$_3$) δ values: 0.40–1.60(7H, m), 3.50–4.60 (3H, m), 7.65(1H, d, J=8.5 Hz), 8.35(1H, d, J=8.5 Hz), 8.60(1H, s).

REFERENCE EXAMPLE 7

(1) In 380 ml of diethyl ether was dissolved 19.0 g of 1-bromo-3,4-di(hydroxymethyl)benzene and to the solution was added 112 g of phosphorus tribromide under ice-cooling, after which the resulting mixture was allowed to stand for 3 days. The reaction mixture was added to 1,000 ml of ice water and the pH was adjusted to 7 with sodium hydrogencarbonate, followed by extraction with 1,000 ml of ethyl acetate. The organic layer thus obtained was washed with a saturated aqueous sodium chloride solution, dried over anhydrous magnesium sulfate, and then distilled under reduced pressure to remove the solvent, whereby 28.5 g of 1-bromo-3,4-di(bromomethyl)benzene were obtained as colorless crystals.

(2) In 70 ml of N,N-dimethylformamide was suspended 3.97 g of sodium hydride (purity: 60%), followed by adding thereto 50 ml of a N,N-dimethylformamide solution containing 8.49 g of p-toluenesulfonamide, and the resulting mixture was stirred at 60° C. for 30 minutes. A solution of 17.0 g of 1-bromo-3,4-di(bromomethyl)benzene in 50 ml of N,N-dimethylformamide was added to the reaction mixture at 60° C. and the resulting mixture was stirred at the same temperature for 1 hour. The reaction mixture obtained was added to 500 ml of ice water and the precipitate was collected by filtration and purified by a column chromatography (eluent: chloroform) to obtain 15.2 g of 5-bromo-2-(p-toluenesulfonyl)isoindoline as colorless crystals.

IR (KBr) cm$^{-1}$: vSO$_2$ 1347, 1164.

NMR (CDCl$_3$) δ values: 2.39(3H, s), 4.56(4H, brs), 6.75–7.90(6H, m).

The following compound was obtained in the same manner as above.

5-Bromo-4-fluoro-2-(p-toluenesulfonyl)isoindoline
IR (KBr) cm$^{-1}$: vSO$_2$ 1343, 1157.
NMR (CDCl$_3$) δ values: 2.41(3H, s), 4.64(4H, brs), 6.60–7.90(7H, m).

REFERENCE EXAMPLE 8

In 25 ml of 47% hydrobromic acid was suspended 5.0 g of 5-bromo-2-(p-toluenesulfonyl)isoindoline, followed by adding thereto 4.0 g of phenol and 15 ml of propionic acid, and the resulting mixture was heated under reflux for 4 hours. The reaction mixture was concentrated under reduced pressure, after which ethanol was added to the resulting residue and the crystals were collected by filtration to obtain 3.5 g of 5-bromoisoindoline hydrobromide. The hydrobromide obtained was suspended in 50 ml of methylene chloride, followed by adding thereto 2.8 g of triethylamine.

Then, 2.4 g of benzyl chloroformate was added dropwise thereto and the resulting mixture was stirred at room temperature for 1 hour. The reaction mixture was added to 50 ml of water and the pH was adjusted to 1 with 6N hydrochloric acid, after which the organic layer was separated. The organic layer obtained was washed with a saturated aqueous sodium chloride solution, dried over anhydrous magnesium sulfate, and then distilled under reduced pressure to remove the solvent. n-Hexane was added to the resulting residue and the crystals were collected by filtration to obtain 3.8 g of colorless 2-benzyloxy-carbonyl-5-bromoisoindoline.

IR (KBr) cm$^{-1}$: vc=o 1705.

NMR (CDCl$_3$) δ values: 4.69(4H, s), 5.20(2H, s), 6.70–7.40(8H, m).

REFERENCE EXAMPLE 9

(1) In 10 ml of tetrahydrofuran was dissolved 1.47 g of (L)-(N-benzyloxycarbonyl)-phenylalanine, followed by adding thereto 1.20 g of 5-bromo-1-methylisoindoline hydrobromide and 0.41 g of triethylamine, and the resulting mixture was stirred for 30 minutes. Then, 1.11 g of 1-hydroxybenzotriazole and 1.03 g of diisopropylcarbodiimide were added to the reaction solution, and the resulting mixture was stirred for 1.5 hours. The reaction mixture obtained was added to a mixed solvent of 20 ml of diethyl ether and 20 ml of water and the pH was adjusted to 1 with 6N hydrochloric acid, after which the organic layer was separated. The organic layer obtained was washed with a saturated aqueous sodium chloride solution, dried over anhydrous magnesium sulfate, and then distilled under reduced pressure to remove the solvent. The resulting residue was subjected to an intermediate-pressure column chromatography (eluent; n-hexane:ethyl acetate=2:1) to separate and purify a diastereomer having a high polarity, whereby 0.78 g of 2-[(N-benzyloxycarbonyl)-(L)-phenylalanine]-5-bromo-1-methylisoindoline as a colorless amorphous solid.

$[\alpha]_D^{29}$=21.3(c=1.0, CHCl$_3$).

IR (KBr) cm$^{-1}$: vc=o 1717, 1654, 1636.

NMR (CDCl$_3$) δ values: 1.32(3H, d, J=6.5 Hz), 2.90–3.20 (2H, m), 3.70–4.00(1H, m), 4.50–5.40(5H, m), 5.60–5.90 (1H, m), 6.80–7.60(13H, m). (2) To 8.50 g of 2-[(N-benzyloxycarbonyl)-(L)-phenylalanine]-5-bromo-1-methylisoindoline was added 170 ml of 6N hydrochloric acid, and the resulting mixture was heated under reflux for 48 hours. The reaction mixture was cooled to room temperature and then added to a mixed solvent of 170 ml of ethyl acetate and 170 ml of water, and the aqueous layer was separated. The aqueous layer obtained was adjusted to pH 12 with a 5N aqueous sodium hydroxide solution, after which chloroform was added thereto and the organic layer was separated. The organic layer obtained was washed with water, dried over anhydrous magnesium sulfate, and then distilled under reduced pressure to remove the solvent. The resulting residue was dissolved in 50 ml of methylene chloride, followed by adding thereto 1.31 g of triethylamine and 2.21 g of benzyl chloroformate under ice-cooling, and the resulting mixture was stirred at room temperature for 3 hours. To the reaction mixture was added 50 ml of ice water and the pH was adjusted to 1.5 with 6N hydrochloric acid, after which the organic layer was separated. The organic layer obtained was washed with water, dried over anhydrous magnesium sulfate, and then distilled under reduced pressure to remove the solvent. The resulting residue was purified by a column chromatography (eluent; n-hexane:ethyl acetate=8:1) to obtain 2.92 g of (−)-2-benzyloxycarbonyl-5-bromo-1-methylisoindoline as an oil.

$[\alpha]_D^{27}$=−10.8 (c=1.3, CHCl$_3$).

IR (neat) cm$^{-1}$: vc=o 1702.

NMR (CDCl$_3$) δ values: 1.30–1.70(3H, m), 4.71(2H, brs), 4.90–5.40 (3H, m), 6.90–7.60(8H, m).

A diastereomer having a low polarity was separated and purified in the same manner as in section (1) and then treated in the same manner as in section (2) to obtain the following compound.

(+)-2-Benzyloxycarbonyl-5-bromo-1-methylisoindoline $[\alpha]_D^{27}$=11.0 (c=1.0, CHCl$_3$).

(3) In 48 ml of methylene chloride was dissolved 16.0 g of the 5-bromo-1-methylisoindoline (derived from the diastereomer having a high polarity) obtained in section (2), and 8.02 g of triethylamine was added thereto. To the resulting solution were added dropwise a solution of 21.0 g of trityl chloride in 80 ml of methylene chloride under ice-cooling over a period of 1 hour, and the resulting mixture was stirred at room temperature for 3 hours. To the reaction mixture was added 48 ml of water, after which the organic layer was separated. The organic layer obtained was washed with water, dried over anhydrous magnesium sulfate, and then distilled under reduced pressure to remove the solvent. Isopropanol was added to the resulting residue and the crystals were collected by filtration to obtain 28.7 g of purplish-red (+)-5-bromo-1-methyl-2-trityliso-indoline.

$[\alpha]_D^{27}$=91.9 (c=1.1, CHCl$_3$).

IR (KBr) cm$^{-1}$: v 1595, 1447, 749, 710.

NMR (CDCl$_3$) δ values: 1.37(3H, d, J=6.5 Hz), 3.80–4.70 (3H, m), 6.45–7.70(18H, m).

REFERENCE EXAMPLE 10

In 24 ml of toluene was suspended 1.20 g of 5-bromo-2-(p-toluenesulfonyl)isoindoline, followed by adding thereto 3.95 g of hexabutyldistannane and 39.4 mg of tetrakis (triphenylphosphine)palladium (0), and the resulting mixture was heated under reflux for 24 hours under a nitrogen atmosphere. The reaction mixture was concentrated under reduced pressure and the resulting residue was purified by a column chromatography (eluent; n-hexane:ethyl acetate= 10:1) to obtain 0.92 g of 2-(p-toluenesulfonyl)-5-tributylstannylisoindoline as an oil.

IR (neat) cm$^{-1}$: vSO$_2$ 1349, 1166.

NMR (CDCl$_3$) δ values: 0.20–2.00(27H, m), 2.40(3H, s), 4.61(4H, brs), 6.50–8.00(7H, m).

The following compound was obtained in the same manner as above.

2-Benzyloxycarbonyl-5-tributylstannylisoindoline

IR (neat) cm$^{-1}$: vc=o 1718, 1709.

NMR (CDCl$_3$) δ values: 0.30–1.70(27H, m), 4.73(4H, s), 5.15(2H, s), 6.80–7.40(8H, m).

REFERENCE EXAMPLE 11

In 45.3 g of 2,3-dimethylnitrobenzene was uspended 0.6 g of iron powder, followed by adding dropwise thereto 57.5 g of bromine on an oil bath at 75° C., and the resulting mixture was stirred at the same temperature for 3.5 hours. The reaction mixture was cooled to room temperature and then added to a mixed solvent of 200 ml of ethyl acetate and 200 ml of water, and the organic layer was separated. The organic layer obtained was washed with an aqueous sodium thiosulfate solution and then a saturated aqueous sodium chloride solution, dried over anhydrous magnesium sulfate, and then distilled under reduced pressure to remove the solvent. The resulting residue was dissolved in 200 ml of methanol and 200 ml of concentrated hydrochloric acid, followed by adding thereto 50.0 g of iron powder by portions, and the resulting mixture was stirred at 70° C. for 30 minutes. The reaction mixture was cooled to room temperature and then added to a mixed solvent of 300 ml of ethyl acetate and 300 ml of water, and the pH was adjusted to 10 with potassium carbonate, after which the organic layer was separated. The organic layer obtained was washed with water and then a saturated aqueous sodium chloride solution, dried over anhydrous magnesium sulfate, and then distilled under reduced pressure to remove the solvent. The resulting residue was purified by a column chromatography (eluent; n-hexane:ethyl acetate=10:1) to obtain 22.6 g of 5-bromo-2,3-dimethylaniline as a colorless oil.

IR (KBr) cm$^{-1}$; $\nu NH_2$ 3384.

NMR (CDCl$_3$) δ values: 1.98(3H, s), 2.20(3H, s), 3.47 (2H, brs), 6.20–6.80(2H, m).

REFERENCE EXAMPLE 12

In 50 ml of 42% borofluoric acid was suspended 5.00 g of 5-bromo-2,3-dimethylaniline, followed by adding dropwise thereto 3.9 ml of an aqueous solution of 1.80 g of sodium nitrite under ice-cooling, and the resulting mixture was stirred at the same temperature for 1 hour. The crystals precipitated were collected by filtration, dried under reduced pressure, and then heated at 60° C. on an oil bath. At the time when a theoretical amount of nitrogen was produced, the reaction mixture was cooled to room temperature and then added to a mixed solvent of 50 ml of ethyl acetate and 50 ml of water, and the organic layer was separated. The organic layer obtained was washed with a saturated aqueous sodium chloride solution, dried over anhydrous magnesium sulfate, and then distilled under reduced pressure to remove the solvent. The resulting residue was purified by a column chromatography (eluent; n-hexane:ethyl acetate=30:1) to obtain 2.90 g of 5-bromo-2,3-dimethylfluorobenzene as a colorless oil.

NMR (CDCl$_3$) δ values: 2.11(3H, d, J=2.0 Hz), 2.24(3H, s), 6.80–7.10(2H, m).

REFERENCE EXAMPLE 13

(1) In 50 ml of carbon tetrachloride was dissolved 4.90 g of 5-bromo-2,3-dimethylfluorobenzene, followed by adding thereto 9.50 g of N-bromosuccinimide and 10 mg of benzoyl peroxide, and the resulting mixture was stirred with heating under reflux for 2 hours. The reaction mixture was cooled to room temperature and then added to 50 ml of water, and the organic layer was separated. The organic layer obtained was washed with a saturated aqueous sodium chloride solution, dried over anhydrous magnesium sulfate, and then distilled under reduced pressure to remove the solvent. n-Hexane was added to the resulting residue and the crystals were collected by filtration to obtain 5.70 g of colorless 5-bromo-2,3-di (bromomethyl)fluorobenzene.

(2) In 30 ml of N,N-dimethylformamide was suspended 1.30 g of sodium hydride (purity: 60%), and 15 ml of a N,N-dimethylformamide solution containing 2.80 g of p-toluenesulfonamide was added thereto at room temperature, after which the resulting mixture was stirred at the same temperature for 30 minutes and then at 60° C. for 1 hour. A solution of 5.70 g of 5-bromo-2,3-di (bromomethyl)fluorobenzene in 15 ml of N,N-dimethylformamide was added to the reaction mixture at 60° C. and the resulting mixture was stirred at the same temperature for 10 minutes. The reaction mixture was added to 200 ml of water and the precipitate was collected by filtration to obtain 2.40 g of 5-bromo-7-fluoro-2-(p-toluenesulfonyl)isoindoline as colorless crystals.

IR (KBr) cm$^{-1}$: $\nu SO_2$ 1343, 1156.

NMR (CDCl$_3$) δ values: 2.41(3H, s), 4.60(4H, brs), 6.50–7.90(6H, m).

The following compounds were obtained in the same manner as above.

5-Bromo-7-methoxy-2-(p-toluenesulfonyl)isoindoline
NMR (CDCl$_3$) δ values: 2.40(3H, s), 3.79(3H, s), 4.52 (4H, brs), 6.70–7.95(6H, m).

5-Bromo-6-fluoro-2-(p-toluenesulfonyl)isoindoline
NMR (CDCl$_3$) δ values: 2.40(3H, s), 4.55(4H, brs), 6.65–7.90(6H, m).

REFERENCE EXAMPLE 14

In 10 ml of xylene was suspended 1.00 g of 5-bromo-7-fluoro-2-(p-toluenesulfonyl)isoindoline, followed by adding thereto 2.70 g of hexabutyldistannane and 19 mg of bis (triphenylphosphine)palladium(II) chloride, and the resulting mixture was heated under reflux for 1 hour under an argon atmosphere. The reaction mixture was concentrated under reduced pressure and the resulting residue was purified by a column chromatography (eluent; n-hexane:ethyl acetate=10:1) to obtain 1.10 g of 7-fluoro-2-(p-toluenesulfonyl)-5-tributylstannylisoindoline as an oil.

IR (neat) cm$^{-1}$: $\nu SO_2$ 1354, 1166.

NMR (CDCl$_3$) δ values: 0.50–1.70(27H, m), 2.40(3H, s), 4.63(4H, brs), 6.70–7.90(6H, m).

The following compounds were obtained in the same manner as above.

4-Fluoro-2-(p-toluenesulfonyl)-5-tributylstannylisoindoline
IR (KBr) cm$^{-1}$: $\nu SO_2$ 1345, 1166.

(−)-2-Benzyloxycarbonyl-1-methyl-5-tributylstannylisoindoline
$[\alpha]_D^{29}$=−4.40 (c=1.0, CHCl$_3$).
IR (neat) cm$^{-1}$: $\nu c=o$ 1708.
NMR (CDCl$_3$) δ values: 0.60–1.90(30H, m), 4.74(2H, brs), 5.00–5.40(3H, m), 7.00–7.60(8H, m).

7-Methoxy-2-(p-toluenesulfonyl)-5-tributylstannylisoindoline
IR (KBr) cm$^{-1}$: $\nu SO_2$ 1343, 1163.
NMR (CDCl$_3$) δ values: 0.50–1.70(27H, m), 2.39(3H, s), 3.80(3H, s), 4.60(4H, brs), 6.65–7.95(6H, m).

REFERENCE EXAMPLE 15

The same procedure as in Reference Example 14 was repeated except for replacing the 5-bromo-7-fluoro-2-(p-toluenesulfonyl)isoindoline by 0.80 g of 5-bromo-6-fluoro-2-(p-toluenesulfonyl)isoindoline to obtain 0.63 g of 6-fluoro-2-(p-toluenesulfonyl)-5-tributylstannylisoindoline.

REFERENCE EXAMPLE 16

The same procedure as in Reference Example 14was repeated except for replacing the 5-bromo-7-fluoro-2-(p-toluenesulfonyl)isoindoline by-2.74 g of (+)-2-benzyloxycarbonyl-5-bromo-1-methylisoindoline to obtain 2.70 g of (+)-2-benzyloxycarbonyl-1-methyl-5-tributyl-stannylisoindoline.

REFERENCE EXAMPLE 17

In 75 ml of anhydrous tetrahydrofuran was dissolved 15.0 g of (+)-5-bromo-1-methyl-2-trityliso-indoline, and the solution was cooled to −72° C. under a nitrogen atmosphere, after which 22.3 ml of a 1.63 M solution of n-butyllithium in n-hexane was added dropwise thereto over a period of 15 minutes, and the resulting mixture was stirred at the same temperature for 1 hour. To the reaction mixture was added dropwise 7.45 g of triisopropoxyborane at −72° C. over a period of 20 minutes, and the resulting mixtuere was stirred at the same temperature for 30 minutes. The reaction mixture was added to 75 ml of ice water and the pH was adjusted to 6.8 with 1N hydrochloric acid, after which the organic layer was separated. The organic layer obtained was washed with water, dried over anhydrous magnesium sulfate, and then distilled under reduced pressure to remove the solvent. Cyclohexane was added to the resulting residue and the crystals were collected by filtration to obtain 11.2 g ofcolorless (+)-1-methyl-2-tritylisoindoline-5-boronic acid.

$[\alpha]_D^{27}$=57.7 (c=1.1, CHCl$_3$).

IR (KBr) cm$^{-1}$: $\nu_{B-O}$ 1356.

NMR (CDCl$_3$) δ values: 1.39(3H, d, J=6.5 Hz), 3.90–4.70 (3H, m), 6.70–7.75(18H, m).

EXAMPLE 1

In 7 ml of xylene was suspended 0.35 g of ethyl 7-bromo-1-cyclopropyl-8-methyl-1,4-dihydro-4-oxoquinoline-3-carboxylate, followed by adding thereto 1.02 g of 7-fluoro-2-(p-toluenesulfonyl)-5-tributyl-stannylisoindoline and 0.07 g of bis(triphenyl-phosphine)palladium(II) chloride, and the resulting mixture was heated under reflux for 2 hours under an argon atmosphere. The reaction mixture was concentrated under reduced pressure and the resulting residue was purified by a column chromatography (eluent; chloroform:ethanol=50:1), after which diethyl ether and ethanol were added to the purified product and the crystals were collected by filtration to obtain 0.35 g of colorless ethyl 1-cyclopropyl-7-[7-fluoro-2-(p-toluenesulfonyl)-isoindolin-5-yl]-8-methyl-1,4-dihydro-4-oxoquinoline-3-carboxylate.

IR (KBr) cm$^{-1}$: νc=o 1724.

NMR (CDCl$_3$) δ values: 0.90–1.70(7H, m), 2.42(3H, s), 2.55(3H, s), 3.70–4.10(1H, m), 4.40(2H, q, J=7.0 Hz), 4.71(4H, s), 6.60–7.90(7H, m), 8.31(1H, d, J=8.5 Hz), 8.69(1H, s).

EXAMPLES 2 to 14

The following compounds were obtained in the same manner as in Example 1.

No. 2: Ethyl 1-cyclopropyl-7-[2-(p-toluenesulfonyl)-isoindolin-5-yl]-8-methyl-1,4-dihydro-4-oxoquinoline-3-carboxylate IR (KBr) cm$^{-1}$: νc=o 1721.

NMR (CDCl$_3$) δ values: 0.70–1.70(7H, m), 2.40(3H, s), 2.53(3H, s), 3.65–4.90(7H, m), 6.90–7.95(8H, m), 8.30(1H, d, J=8.0 Hz), 8.68(1H, s).

No. 3: Ethyl 1-cyclopropyl-8-fluoro-7-[2-(p-toluenesulfonyl)isoindolin-5-yl]-1,4-dihydro-4-oxoquinoline-3-carboxylate IR (KBr) cm$^{-1}$: νc=o 1730, 1680.

NMR (CDCl$_3$) δ values: 0.90–1.60(7H, m), 2.41(3H, s), 3.60–4.00(1H, m), 4.40(2H, q, J=7.0 Hz), 4.70(4H, s), 6.80–7.80(8H, m), 8.30(1H, d, J=8.5 Hz), 8.59(1H, s).

No. 4: Ethyl 7-[2-(benzyloxycarbonyl)isoindolin-5-yl]-1-cyclopropyl-8-methoxy-1,4-dihydro-4-oxoquinoline-3-carboxylate IR (KBr) cm$^{-1}$: νc=o 1716.

NMR (CDCl$_3$) δ values: 0.70–1.70(7H, m), 3.36(3H, s), 3.70–4.10(1H, 5 m), 4.40(2H, q, J=7.5 Hz), 4.83(4H, s), 5.23(2H, s), 6.90–7.70(9H, m), 8.28(1H, d, J=8.5 Hz), 8.63(1H, s).

No. 5: Ethyl 7-[2-(benzyloxycarbonyl)isoindolin-5-yl]-1-cyclopropyl-8-trifluoromethyl-1,4-dihydro-4-oxoquinoline-3-carboxylate IR (KBr) cm$^{-1}$: νc=o 1729.

NMR (CDCl$_3$) δ values: 0.45–1.70(7H, m), 3.65-4.10(1H, m), 4.41(2H, q, J=7.5 Hz), 4.84(4H, s), 5.23(2H, s), 6.85–7.80(9H, m), 8.25–8.80(2H, m).

No. 6: Ethyl 1-cyclopropyl-7-[7-fluoro-2-(p-toluenesulfonyl)isoindolin-5-yl]-8-methoxy-1,4-dihydro-4-oxoquinoline-3-carboxylate IR (KBr) cm$^{-1}$: νc=o 1732, 1691.

NMR (CDCl$_3$) δ values: 0.90–1.60(7H, m), 2.42(3H, s), 3.36(3H, s), 3.70–4.10(1H, m), 4.40(2H, q, J=7.0 Hz), 4.72(4H, s), 7.00–7.90(7H, m), 8.27(1H, d, J=8.5 Hz), 8.62(1H, s).

No. 7: Ethyl 1-cyclopropyl-8-difluoromethoxy-7-[2-(p-toluenesulfonyl)isoindolin-5-yl]-1,4-dihydro-4-oxoquinoline-3-carboxylate IR (KBr) cm$^{-1}$: νc=o 1731.

No. 8: Ethyl 1-cyclopropyl-8-difluoromethoxy-7-[7-fluoro-2-(p-toluenesulfonyl)isoindolin-5-yl]-1,4-dihydro-4-oxoquinoline-3-carboxylate IR (KBr) cm$^{-1}$: νc=o 1724.

NMR (CDCl$_3$) δ values: 0.90–1.60(7H, m), 2.42(3H, s), 3.80–4.20(1H, m), 4.40(2H, q, J=7.0 Hz), 4.72(4H, s), 5.88(1H, t, J=72.5 Hz), 7.10–7.90(7H, m), 8.41(1H, d, J=8.5 Hz), 8.64(1H, s).

No. 9: Ethyl 1-cyclopropyl-7-[4-fluoro-2-(p-toluenesulfonyl)isoindolin-5-yl]-8-methoxy-1,4-dihydro-4-oxoquinoline-3-carboxylate NMR (CDCl$_3$) δ values: 0.70–1.80(7H, m), 2.42(3H, s), 3.36(3H, s), 3.70–4.10(1H, m), 4.40(2H, q, J=7.0 Hz), 4.73(4H, s), 6.80–7.95(7H, m), 8.27(1H, d, J=8.5 Hz), 8.63(1H, s).

No. 10: Ethyl 1-cyclopropyl-8-difluoromethoxy-7-[7-methoxy-2-(p-toluenesulfonyl)isoindolin-5-yl]-1,4-dihydro-4-oxoquinoline-3-carboxylate IR (KBr) cm$^{-1}$: νc=o 1698.

NMR (CDCl$_3$) δ values: 0.70–1.60(7H, m), 2.40(3H, s), 3.85(3H, s), 3.90–4.70(7H, m), 5.85(1H, t, J=74 Hz), 6.70–7.40(6H, mn), 7.79(1H, d, J=8.5 Hz), 8.41(1H, d, J=8.5 Hz), 8.65(1H, s).

No. 11: Ethyl (±)-1-cyclopropyl-8-methoxy-7-[1-methyl-2-(p-toluenesulfonyl)isoindolin-5-yl]-1,4-dihydro-4-oxoquinoline-3-carboxylate IR (KBr) cm$^{-1}$: νc=o 1732.

NMR (CDCl$_3$) δ values: 0.70–1.90(10H, m), 2.37(3H, s), 3.29(3H, s), 3.70–5.20(6H, m), 7.00–7.90(8H, m), 8.13(1H, d, J=8.5 Hz), 8.60(1H, s).

No. 12: Ethyl (±)-1-cyclopropyl-8-difluoromethoxy-7-[1-methyl-2-(p-toluenesulfonyl)isoindolin-5-yl]-1,4-dihydro-4-oxoquinoline-3-carboxylate IR (KBr) cm$^{-1}$: νc=o 1726.

NMR (CDCl$_3$) δ values: 0.70–1.90(10H, m), 2.39(3H, s), 3.60–5.20(6H, m), 5.80(1H, t, J=74 Hz), 7.00–7.90(8H, m), 8.41(1H, d, J=8.5 Hz), 8.65(1H, s).

No. 13: Ethyl (+)-1-cyclopropyl-8-difluoromethoxy-7-[2-benzyloxycarbonyl-1-methylisoindolin-5-yl]-1,4-dihydro-4-oxoquinoline-3-carboxylate $[\alpha]_D^{27}$=6.70 (c=1.0, CHCl$_3$).

IR (KBr) cm$^{-1}$: νc=o 1733, 1700.

NMR (CDCl$_3$) δ values: 0.80–1.80(10H, m), 3.90–4.20 (1H, m), 4.41(2H, q, J=7.0 Hz), 4.83(2H, brs), 5.10–5.40 (3H, m), 5.87(1H, t, J=75 Hz), 7.20–7.70(9H, m), 8.44(1H, d, J=8.5 Hz), 8.68(1H, s).

No. 14: Ethyl (−)-1-cyclopropyl-8-difluoromethoxy-7-[2-benzyloxycarbonyl-1-methylisoindolin-5-yl3-1,4-dihydro-4-oxoquinoline-3-carboxylate $[\alpha]_D^{27}=-6.84$ (c=0.8, CHCl$_3$).

IR (KBr) cm$^{-1}$: νc=o 1732, 1703.

EXAMPLE 15

In the same manner as in Example 1, 0.45 g of ethyl 7-bromo-8-chloro-1-cyclopropyl-1,4-dihydro-4-oxoquinoline-3-carboxylate was reacted with 1.02 g of 2-(p-toluenesulfonyl)-5-tributylstannylisoindoline to obtain 0.54 g of ethyl 8-chloro-1-cyclopropyl-7-[2-(p-toluenesulfonyl) isoindolin-5-yl]-1,4-dihydro-4-oxoquinoline-3-carboxylate.

EXAMPLE 16

In the same manner as in Example 1, 0.23 g of ethyl 7-bromo-1-cyclopropyl-8-methoxy-1,4-dihydro-4-oxoquinoline-3-carboxylate was reacted with 0.63 g of 6-fluoro-2-(p-toluenesulfonyl)-5-tributylstannyliso-indoline to obtain 0.25 g of ethyl 1-cyclopropyl-7-[6-fluoro-2-(p-toluenesulfonyl)isoindolin-5-yl]-8-methoxy-1,4-dihydro-4-oxoquinoline-3-carboxylate.

EXAMPLE 17

In 7 ml of toluene was suspended 0.70 g of ethyl 7-bromo-1-cyclopropyl-8-difluoromethoxy-1,4-dihydro-4-oxoquinoline-3-carboxylate, followed by adding thereto 3 ml of ethanol, 1.74 ml of a 2 M aqueous sodium carbonate solution, 0.80 g of (+)-1-methyl-2-trityliso-indoline-5-boronic acid and 0.05 g of bis(triphenyl-phosphine) palladium(II) chloride, and the resulting mixture was heated under reflux for 2 hours under a nitrogen atmosphere. The reaction mixture was added to a mixed solvent of 10 ml of ethyl acetate and 10 ml of water, and the organic layer was separated. The organic layer obtained was washed with a saturated aqueous sodium chloride solution, dried over anhydrous magnesium sulfate, and then distilled under reduced pressure to remove the solvent. The resulting residue was purified by a column chromatography (eluent; n-hexane:ethyl acetate=1:1) to obtain 0.72 g of ethyl (+)-1-cyclopropyl-8-difluoromethoxy-7-(1-methyl-2-tritylisoindolin-5-yl)-1,4-dihydro-4-oxoquinoline-3-carboxylate as colorless crystals.

$[\alpha]_D^{27}=32.0$ (c=1.0, CHCl$_3$).

IR (KBr) cm$^{-1}$: νc=o 1734, 1691.

NMR (CDCl$_3$) δ values: 0.80–1.90(10H, m), 3.90–4.90 (6H, m), 5.51(1H, t, J=75 Hz), 6.70–8.00(19H, m), 8.35(1H, d, J=8.0 Hz), 8.66(1H, s).

EXAMPLE 18

In 3.3 ml of ethanol was suspended 0.33 g of ethyl 1-cyclopropyl-7-[7-fluoro-2-(p-toluenesulfonyl)-isoindolin-5-yl)-8-methyl-1,4-dihydro-4-oxoquinoline-3-carboxylate, followed by adding thereto 3.3 ml of a 1N aqueous sodium hydroxide solution and 3.3 ml of dioxane, and the resulting mixture was stirred at 40° C. for 30 minutes. To the reaction mixture was added 3.3 ml of 1N hydrochloric acid and the crystals were collected by filtration to obtain 0.31 g of colorless 1-cyclopropyl-7-[7-fluoro-2-(p-toluenesulfonyl) isoindolin-5-yl]-8-methyl-1,4-dihydro-4-oxoquinoline-3-carboxylic acid.

IR (KBr) cm$^{-1}$: νc=o 1725.

NMR (CDCl$_3$) δ values: 0.90–1.40(4H, m), 2.42(3H, s), 2.63(3H, s), 3.90–4.30(1H, m), 4.72(4H, s), 6.70–7.90(7H, m), 8.33(1H, d, J=8.5 Hz), 8.97(1H, s), 14.50(1H, s).

EXAMPLES 19 To 30

The following compounds were obtained in the same manner as in Example 18.

No. 19: 1-Cyclopropyl-8-methyl-7-[2-(p-toluene-sulfonyl) isoindolin-5-yl]-1,4-dihydro-4-oxoquinoline-3-carboxylic acid IR (KBr) cm$^{-1}$: νc=o 1718.

NMR (CDCl$_3$) δ values: 0.70–1.80(4H, m), 2.42(3H, s), 2.62(3H, s), 3.80–4.30(1H, m), 4.69(4H, s), 6.85–7.95(8H, m), 8.34(1H, d, J=8.5 Hz), 8.97(1H, s), 14.59(1H, brs).

No. 20: 1-Cyclopropyl-8-fluoro-7-(2-(p-toluene-sulfonyl) isoindolin-5-yl]-1,4-dihydro-4-oxoquinoline-3-carboxylic acid IR (KBr) cm$^{-1}$: νc=o 1727.

NMR (CDCl$_3$) δ values: 0.90–1.60(4H, m), 2.41(3H, s), 3.80–4.20(1H, m), 4.70(4H, s), 7.00–7.90(8H, mn), 8.33 (1H, d, J=9.0 Hz), 8.88(1H, s), 14.37(1H, brs).

No. 21: 7-[2-(Benzyloxycarbonyl)isoindolin-5-yl]-1-cyclopropyl-8-methoxy-1,4-dihydro-4-oxoquinoline-3-carboxylic acid IR (KBr) cm$^{-1}$: νc=o 1724.

NMR (CDCl$_3$) δ values: 0.80–1.70(4H, m), 3.39(3H, s), 3.80–4.30(1H, m), 4.84(4H, s), 5.23(2H, s), 6.90–7.70(9H, m), 8.30(1H, d, J=8.5 Hz), 8.91(1H, s), 14.5(1H, brs).

No. 22: 7-[2-(Benzyloxycarbonyl)isoindolin-5-yl]-1-cyclopropyl-8-trifluoromethyl-1,4-dihydro-4-oxoquinoline-3-carboxylic acid IR (KBr) cm$^{-1}$: νc=o 1716.

NMR (CDCl$_3$) δ values: 0.40–1.70(4H, m), 3.80–4.45 (1H, m), 4.85(4H, s), 5.23(2H, s), 6.95–7.75(9H, m), 8.70 (1H, d, J=8.0 Hz), 8.97(1H, s), 13.9(1H, brs).

No. 23: 1-Cyclopropyl-7-[7-fluoro-2-(p-toluene-sulfonyl) isoindolin-5-yl]-8-methoxy-1,4-dihydro-4-oxoquinoline-3-carboxylic acid IR (KBr) cm$^{-1}$: νc=o 1724.

NMR (CDCl$_3$) δ values: 1.00–1.40(4H, m), 2.42(3H, s), 3.40(3H, s), 3.90–4.30(1H, m), 4.73(4H, s), 7.00–7.90(7H, m), 8.23(1H, d, J=8.5 Hz), 8.90(1H, s), 14.48(1H, brs).

No. 24: 1-Cyclopropyl-8-difluoromethoxy-7-[2-(p-toluenesulfonyl)isoindolin-5-yl]-1,4-dihydro-4-oxoquinoline-3-carboxylic acid IR (KBr) cm$^{-1}$: νc=o 1719.

No. 25: 1-Cyclopropyl-8-difluoromethoxy-7-[7-fluoro-2-(p-toluenesulfonyl)isoindolin-5-yl]-1,4-dihydro-4-oxoquinoline-3-carboxylic acid IR (KBr) cm$^{-1}$: νc=o 1727.

NMR (CDCl$_3$) δ values: 0.90–1.50(4H, mn), 2.42(3H, s), 4.00–4.40(1H, m), 4.73(4H, s), 5.94(1H, t, J=72.5 Hz), 7.10–7.90(7H, m), 8.45(1H, d, J=9.0 Hz), 8.92(1H, s), 14.17(1H, brs).

No. 26: 1-Cyclopropyl-7-[4-fluoro-2-(p-toluene-sulfonyl) isoindolin-5-yl]-8-methoxy-1,4-dihydro-4-oxoquinoline-3-carboxylic acid NMR (CDCl$_3$) δ values: 0.70–1.80(4H, m), 2.43(3H, s), 3.40(3H, s), 3.80–4.20(1H, m), 4.74(4H, s), 6.80–7.90(7H, m), 8.30(1H, d, J=8.5 Hz), 8.92(1H, s), 14.4(1H, brs).

No. 27: (±)-1-Cyclopropyl-8-methoxy-7-[1-methyl-2-(p-toluenesulfonyl)isoindolin-5-yl]-1,4-dihydro-4-oxoquinoline-3-carboxylic acid NMR (d$_1$-TFA) δ values: 1.00–1.80(7H, m), 2.31(3H, s), 3.40(3H, s), 4.30–5.40(4H, m), 7.00–8.00(8H, m), 8.40(1H, d, J=8.0 Hz), 9.35(1H, s).

No. 28: (+)-1-Cyclopropyl-8-difluoromethoxy-7-(1-methyl-2-(p-toluenesulfonyl)isoindolin-5-yl]-1,4-dihydro-4-oxoquinoline-3-carboxylic acid IR (KBr) cm$^{-1}$: νc=o 1733.

NMR (d$_1$-TFA) δ values: 1.00–1.90(7H, m), 2.35(3H, s), 4.30–5.40(4H, m), 5.94(1H, t, J=74 Hz), 6.90–8.10(8H, m), 8.63(1H, d, J=8.5 Hz), 9.50(1H, s).

No. 29: (+)-1-Cyclopropyl-8-difluoromethoxy-7-[2-benzyloxycarbonyl-1-methylisoindolin-5-yl]-1,4-dihydro-4-oxoquinoline-3-carboxylic acid $[\alpha]_D^{29}$=4.50 (c=0.2, CHCl$_3$).

IR (KBr) cm$^{-1}$: vc=o 1718.

NMR (CDCl$_3$) δ values: 1.00–2.00(7H, m), 4.10–4.40 (1H, m), 4.84(2H, brs), 5.10–5.60(3H, m), 5.91(1H, t, J=75 Hz), 7.20–8.00(9H, m), 8.47(1H, d, J=8.5 Hz), 8.96(1H, s).

No. 30: (−)-1-Cyclopropyl-8-difluoromethoxy-7-[2-benzyloxycarbonyl-1-methylisoindolin-5-yl]-1,4-dihydro-4-oxoquinoline-3-carboxylic acid $[\alpha]_D^{28}$=−5.86 (c=1.1, CHCl$_3$).

IR (KBr) cm$^{-1}$: vc=o 1716, 1700.

EXAMPLE 31

In the same manner as in Example 18, 0.50 g of ethyl 8-chloro-1-cyclopropyl-7-[2-(p-toluenesulfonyl)-isoindolin-5-yl]-1,4-dihydro-4-oxoquinoline-3-carboxylate was hydrolyzed to obtain 0.47 g of 8-chloro-1-cyclopropyl-7-[2-(p-toluenesulfonyl)isoindolin-5-yl]-1,4-dihydro-4-oxoquinoline-3-carboxylic acid.

EXAMPLE 32

In the same manner as in Example 18, 0.25 g of ethyl 1-cyclopropyl-7-[6-fluoro-2-(p-toluenesulfonyl)-isoindolin-5-yl]-8-methoxy-1,4-dihydro-4-oxoquinoline-3-carboxylate was hydrolyzed to obtain 0.10 g of 1-cyclo-propyl-7-[6-fluoro-2-(p-toluenesulfonyl)isoindolin-5-yl]-8-methoxy-1,4-dihydro-4-oxoquinoline-3-carboxylic acid.

EXAMPLE 33

In 10 ml of methylene chloride was suspended 0.28 g of ethyl 1-cyclopropyl-8-difluoromethoxy-7-[7-methoxy-2-(p-toluenesulfonyl)isoindolin-5-yl]-1,4-dihydro-4-oxoquinoline-3-carboxylate, and the suspension was cooled to −30° C., after which 1.3 ml of 1.0 M solution of boron tribromide in methylene chloride was added dropwise thereto over a period of 5 minutes, and the resulting mixture was stirred at 0° C. for 2 hours. The reaction mixture was added to a mixed solvent of 10 ml of chloroform and 10 ml of water, and the organic layer was separated. The organic layer obtained was washed with water, dried over anhydrous magnesium sulfate, and then distilled under reduced pressure to remove the solvent. The resulting residue was purified by a column chromatography (eluent; chloroform:acetone=5:1) and the crystals thus obtained were suspended in 1.5 ml of ethanol and 1.5 ml of dioxane, after which 0.74 ml of a 1N aqueous sodium hydroxide solution was added thereto and the resulting mixture was stirred at 60° C. for 30 minutes. To the reaction mixture was added 0.74 ml of 1N hydrochloric acid and the crystals were collected by filtration to obtain 0.12 g of light-brown 1-cyclopropyl-8-difluoromethoxy-7-[7-hydroxy-2-(p-toluenesulfonyl)isoindolin-5-yl]-1,4-dihydro-4-oxoquinoline-3-carboxylic acid.

IR (KBr) cm$^{-1}$: vc=o 1700.

NMR (d$_6$-DMSO) δ values: 0.90–1.40(7H, m), 2.49(3H, s), 3.90–4.70(5H, m), 6.56(1H, t, J=74 Hz), 6.92(2H, s), 7.35-7.85(5H, m), 8.31(1H, t, J=8.5 Hz), 8.86(1H, s), 9.94 (1H, s).

EXAMPLE 34

In 3.0 ml of 47% hydrobromic acid was suspended 0.30 g of 1-cyclopropyl-7-[7-fluoro-2-(p-toluenesulfonyl) isoindolin-5-yl]-8-methyl-1,4-dihydro-4-oxoquinoline-3-carboxylic acid, followed by adding thereto 0.16 g of phenol and 1.8 ml of propionic acid, and the resulting mixture was heated at 100° C. for 10 hours under a nitrogen atmosphere. The reaction mixture was concentrated under reduced pressure, after which ethanol was added to the resulting residue and the crystals were collected by filtration to obtain 0.21 g of colorless 1-cyclopropyl-7-(7-fluoroisoindolin-5-yl)-8-methyl-1,4-dihydro-4-oxoquinoline-3-carboxylic acid hydrobromide. The hydrobromide obtained was suspended in 1.3 ml of ethanol and dissolved in 2.6 ml of a 0.5 N aqueous sodium hydroxide solution, after which carbon dioxide was bubbled into the resulting solution and the crystals were collected by filtration to obtain 0.10 g of colorless 1-cyclopropyl-7-(7-fluoroisoindolin-5-yl)-8-methyl-1,4-dihydro-4-oxoquinoline-3-carboxylic acid.

IR (KBr) cm$^{-1}$: vc=o 1721.

NMR (d$_1$-TFA) δ values: 1.20–1.80(4H, m), 2.98(3H, s), 4.50–4.90(1H, m), 5.08(4H, s), 7.00–7.40(2H, m), 7.88(1H, d, J=8.5 Hz), 8.70(1H, d, J=8.5 Hz), 9.67(1H, s).

EXAMPLES 35 to 45

The following compounds were obtained in the same manner as in Example 34.

No. 35: 1-Cyclopropyl-7-(isoindolin-5-yl)-8-methyl-1,4-dihydro-4-oxoquinoline-3-carboxylic acid IR (KBr) cm$^{-1}$: vc=o 1625.

NMR (d$_1$-TFA) δ values: 0.90–2.05(4H, m), 2.96(3H, s), 4.30–5.35(5H, m), 7.20–8.00(4H, m), 8.69(1H, d, J=9.0 Hz), 9.65(1H, s).

No. 36: 1-Cyclopropyl-8-fluoro-7-(isoindolin-5-yl)-1,4-dihydro-4-oxoquinoline-3-carboxylic acid IR (KBr) cm$^{-1}$: vc=o 1647.

NMR (d$_1$-TFA) δ values: 1.20–1.80(4H, m), 4.30–4.70 (1H, m), 5.03(4H, s), 7.30–8.20(4H, m), 8.68(1H, d, J=9.5 Hz), 9.53(1H, s).

No. 37: 8-Chloro-1-cyclopropyl-7-(isoindolin-5-yl)-1,4-dihydro-4-oxoquinoline-3-carboxylic acid IR (KBr) cm$^{-1}$: vc=o 1637.

NMR (d$_1$-TFA) δ values: 1.10–1.90(4H, m), 4.30–5.30 (5H, m), 7.40–8.50(4H, m), 8.78(1H, d, J=9.0 Hz), 9.70(1H, s).

No. 38: 1-Cyclopropyl-7-(7-fluoroisoindolin-5-yl)-8-methoxy-1,4-dihydro-4-oxoquinoline-3-carboxylic acid IR (KBr) cm$^{-1}$: vc=o 1724.

NMR (d$_1$-TFA) δ values: 1.10–1.70(4H, m), 3.65(3H, s), 4.40–4.90(1H, m), 5.08(4H, s), 7.30–7.70(2H, m), 8.00(1H, d, J=9.0 Hz), 8.61(1H, d, J=9.0 Hz), 9.54(1H, s).

No. 39: 1-Cyclopropyl-8-difluoromethoxy-7-(isoindolin-5-yl)-1,4-dihydro-4-oxoquinoline-3-carboxylic acid IR (KBr) cm$^{-1}$: vc=o 1607.

NMR (d$_1$-TFA) δ values: 1.00–1.90(4H, m), 4.40–5.10 (5H, m), 6.17(1H, t, J=73.0 Hz), 7.40–7.80(3H, m), 8.09(1H, d, J=9.0 Hz), 8.77(1H, d, J=9.0 Hz), 9.60(1H, s).

No. 40: 1-Cyclopropyl-8-difluoromethoxy-7-(7-fluoroiso-indolin-5-yl)-1,4-dihydro-4-oxoquinoline-3-carboxylic acid IR (KBr) cm$^{-1}$: vc=o 1720.

NMR (d$_1$-TFA) δ values: 1.00–1.90(4H, m), 4.50–4.90 (1H, m), 5.08(4H, s), 6.28(1H, t, J=72.5 Hz), 7.30–7.70(2H, m), 8.08(1H, d, J=9.0 Hz), 8.80(1H, d, J=9.0 Hz), 9.63(1H, s).

No. 41: 1-Cyclopropyl-7-(6-fluoroisoindolin-5-yl)-8-methoxy-1,4-dihydro-4-oxoquinoline-3-carboxylic acid IR (KBr) cm$^{-1}$: vc=o 1625.

No. 42: 1-Cyclopropyl-7-(4-fluoroisoindolin-5-yl)-8-methoxy-1,4-dihydro-4-oxoquinoline-3-carboxylic acid IR (KBr) cm$^{-1}$: vc=o 1718.

No. 43: 1-Cyclopropyl-8-difluoromethoxy-7-(7-hydroxy-isoindolin-5-yl)-1,4-dihydro-4-oxoquinoline-3-carboxylic acid IR (KBr) cm$^{-1}$: νc=o 1611.

NMR (d$_6$-DMSO) δ values: 0.80–1.40(4H, m), 3.80–4.40 (5H, m), 6.54(1H, t, J=74 Hz), 6.90(2H, s), 7.62(1H, d, J=8.5 Hz), 8.32(1H, d, J=8.5 Hz), 8.86(1H, s).

No. 44: (±)-1-Cyclopropyl-8-methoxy-7-(1-methylisoindolin-5-yl)-1,4-dihydro-4-oxoquinoline-3-carboxylic acid IR (KBr) cm$^{-1}$: νc=o 1718.

NMR (d$_1$-TFA) δ values: 1.20–2.30(7H, m), 3.63(3H, s), 4.40–5.60(4H, m), 7.30–8.15(4H, m), 8.63(1H, d, J=9.0 Hz), 9.56(1H, s).

No. 45: (±)-1-Cyclopropyl-8-difluoromethoxy-7-(1-methylisoindolin-5-yl )-1,4-dihydro-4-oxoquinoline-3-carboxylic acid IR (KBr) cm$^{-1}$: νc=o 1636.

NMR (d$_1$-TFA) δ values: 1.10–2.20(7H, m), 4.40–5.70 (4H, m), 6.15(1H, t, J=74 Hz), 7.20–8.25(4H, m), 8.73(1H, d, J=8.5 Hz), 9.63(1H, s).

EXAMPLE 46

In 14 ml of acetic acid and 140 mg of 5% palladium-carbon was suspended 140 mg of 7-[2-(benzyl-oxycarbonyl) isoindolin-5-yl]-1-cyclopropyl-8-methoxy-1,4-dihydro-4-oxoquinoline-3-carboxylic acid, and the suspension was stirred at room temperature for 2 hours under a hydrogen atomsphere. The reaction mixture was filtered and the filtrate was concentrated under reduced pressure. Ethanol and diethyl ether were added to the resulting residue and the crystals were collected by filtration. To the crystals collected were added 0.8 ml of ethanol, 0.8 ml of a 1N aqueous sodium hydroxide solution and 0.8 ml of water to dissolve the crystals, after which carbon dioxide was bubbled into the resulting solution and the crystals were collected by filtration to obtain 74 mg of colorless 1-cyclopropyl-7-(isoindolin-5-yl)-8-methoxy-1,4-dihydro-4-oxoquinoline-3-carboxylic acid.

IR (KBr) cm$^{-1}$: νc=o 1628.

NMR (d$_1$-TFA) δ values: 1.10–1.80(4H, m), 3.62(3H, s), 4.40–5.20(5H, m), 7.40–8.30(4H, m), 8.61(1H, d, J=9.0 Hz), 9.55(1H, s).

EXAMPLES 47 to 49

The following compounds were obtained in the same manner as in Example 46.

No. 47: 1-Cyclopropyl-7-(isoindolin-5-yl)-8-trifluoromethyl-1,4-dihydro-4-oxoquinoline-3-carboxylic acid IR (KBr) cm$^{-1}$: νc=o 1638.

NMR (d$_1$-TFA) δ values: 0.50–2.00(4H, m), 4.35–5.45 (5H, m), 7.20–8.40(4H, m), 8.90(1H, d, J=8.0 Hz), 9.70 (1H, s).

No. 48: (+)-1-Cyclopropyl-8-difluoromethoxy-7-(1-methylisoindolin-5-yl )-1,4-dihydro-4-oxoquinoline-3-carboxylic acid

[α]$_D^{28}$=+5.26 (c=0.5, 0.1N NaOH).

IR (KBr) cm$^{-1}$: νC=o 1630.

No. 49: (−)-1-Cyclopropyl--8-difluoromethoxy-7-(1-methylisoindolin-5-yl)-1,4-dihydro-4-oxoquinoline-3-carboxylic acid

[α]$_D^{29}$=−5.20 (c=0.5, 0.1N NaOH).

IR (KBr) cm$^{-1}$: νc=o 1630.

NMR (d$_1$-TFA) δ values: 1.20–2.10(7H, m), 4.60–5.20 (3H, m), 5.20–5.60(1H, m), 6.20(1H, t, J=73 Hz), 7.60–8.00 (3H, m), 8.12(1H, d, J=8.5 Hz), 8.80(1H, d, J=8.5 Hz), 9.65(1H, s).

EXAMPLE 50

In 4 ml of ethanol was suspended 1.00 g of ethyl (−)-1-cyclopropyl-8-difluoromethoxy-7-(1-methyl-2-tritylisoindolin-5-yl)-1,4-dihydro-4-oxoquinoline-3-carboxylate, followed by adding thereto 0.26 ml of 6N hydrochloric acid, and the resulting mixture was stirred at room temperature for 30 minutes. The reaction mixture was filtered, after which 0.75 ml of a 5N aqueous sodium hydroxide solution was added to the filtrate and the resulting mixture was stirred at room temperature for 1 hour. To the reaction mixture was added 16 ml of water, followed by filtration. Carbon dioxide was bubbled into the filtrate and the crystals were collected by filtration to obtain 0.56 g of light-yellow (−)-1-cyclopropyl-8-difluoromethoxy-7-(1-methyl-isoindolin-5-yl)-1,4-dihydro-4-oxoquinoline-3-carboxylic acid.

Physical properties of this compound were the same as those of the compound obtained in Example 49.

EXAMPLE 51

To 100 mg of 1-cyclopropyl-7-(isoindolin-5-yl)-8-methoxy-1,4-dihydro-4-oxoquinoline-3-carboxylic acid were added 1 ml of formic acid and 65 mg of formalin, and the resulting mixture was heated under reflux for 1 hour, after which the solvent was distilled under reduced pressure to remove the solvent. To the resulting residue was added 5 ml of water, and the resulting mixture was adjusted to pH 7 with a saturated aqueous sodium hydrogencarbonate solution and extracted with five 5-ml portions of chloroform. The chloroform layer obtained was dried over anhydrous magnesium sulfate and then distilled under reduced pressure to remove the solvent. To the resulting residue were added ethanol and diethyl ether, and the crystals were collected by filtration. To the crystals collected were added 1 ml of ethanol, 1 ml of a 1N aqueous sodium hydroxide solution and 1 ml of water to dissolve the crystals, after which carbon dioxide was bubbled into the resulting solution and the crystals were collected by filtration to obtain 76 mg of light-yellow 1-cyclopropyl-8-methoxy-7-(2-methylisoindolin-5-yl)-1,4-dihydro-4-oxoquinoline-3-carboxylic acid.

IR (KBr) cm$^{-1}$: νc=o 1726.

NMR (d$_1$-TFA) δ values: 1.10–1.80(4H, m), 3.37(3H, s), 3.60(3H, s), 4.30–5.50(5H, m), 7.40–8.10(4H, m), 8.61(1H, d, J=9.0 Hz), 9.54(1H, s).

EXAMPLE 52

In the same manner as in Example 51, 1-cyclopropyl-8-difluoromethoxy-7-(2-methylisoindolin-5-yl)-1,4-dihydro-4-oxoquinoline-3-carboxylic acid was obtained.

IR (KBr) cm$^{-1}$: νc=o 1723.

NMR (d$_1$-TFA) δ values: 1.10–1.90(4H, m), 3.37(3H, s), 4.30–5.50(5H, m), 6.21(1H, t, J=72 Hz), 7.20–8.20(4H, m), 8.79(1H, d, J=9.0 Hz), 9.62(1H, s).

INDUSTRIAL APPLICABILITY

The quinolone derivatives or their salts of the present invention exhibit a strong antibacterial activity against Gram-positive bacteria and Gram-negative bacteria, particularly against MRSA and are very safe compounds. Therefore, they are useful as agents for curing various infectious diseases.

We claim:

1. A quinolonecarboxylic acid derivative represented by the general formula, or its salt:

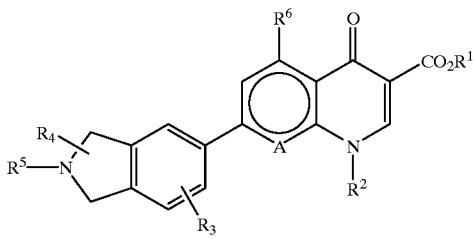

wherein $R^1$ represents a hydrogen atom or a carboxyl-protecting group; $R^2$ represents a substituted or unsubstituted alkyl, alkenyl, cycloalkyl, aryl or heterocyclic group; $R^3$ is selected from the group consisting of a hydrogen atom, halogen atom, a substituted or unsubstituted alkyl, alkenyl, cycloalkyl, aryl, alkoxy or alkylthio group, a nitro group, a cyano group, an acyl group, a protected or unprotected hydroxyl group, and a protected or unprotected, or substituted or unsubstituted amino group; $R^4$ is selected from the group consisting of a hydrogen atom, a halogen atom, a substituted or unsubstituted alkyl, alkenyl, cycloalkyl, aralkyl, aryl, alkoxy or alkylthio group, a protected or unprotected hydroxyl or imino group, a protected or unprotected, or substituted or unsubstituted amino group, an alkylidene group, an oxo group and a group forming a cycloalkane ring together with the carbon atom to which $R^4$ is bonded; $R^5$ represents a hydrogen atom or a substituted or unsubstituted alkyl, cycloalkyl, alkylsulfonyl, arylsulfonyl, acyl or aryl group; $R^6$ represents a hydrogen atom, a halogen atom, a substituted or unsubstituted alkyl, alkoxy or alkylthio group, a protected or unprotected hydroxyl or amino group, or a nitro group; and A represents CH or C-Y in which Y represents a halogen atom, a substituted or unsubstituted alkyl, alkoxy or alkylthio group, or a protected or unprotected hydroxyl group.

2. The quinolonecarboxylic acid derivative or its salt according to claim 1, wherein $R^2$ represents a substituted or unsubstituted lower alkyl, lower alkenyl, cycloalkyl, aryl or heterocyclic group; $R^3$ is selected from the group consisting of a hydrogen atom, a halogen atom, a substituted or unsubstituted lower alkyl, lower alkenyl, cycloalkyl, aryl, lower alkoxy or lower alkylthio group, a nitro group, a cyano group, an acyl group, a protected or unprotected hydroxyl group, and a protected or un protected, or substituted or unsubstituted amino group; $R^4$ is selected from the group consisting of a hydrogen atom, a halogen atom, a substituted or unsubstituted lower alkyl, lower alkenyl, cycloalkyl, aralkyl, aryl, lower alkoxy or lower alkylthio group, a protected or unprotected hydroxyl or imino group, a protected or unprotected, or substituted or unsubstituted amino group, a lower alkylidene group, an oxo group and a group forming a cycloalkane ring together with the carbon atom to which $R^4$ is bonded; $R^5$ represents a hydrogen atom or a substituted or unsubstituted lower alkyl, cycloalkyl, lower alkylsulfonyl, arylsulfonyl, acyl or aryl group; $R^6$ represents a hydrogen atom, a halogen atom, a substituted or unsubstituted lower alkyl, lower alkoxy or lower alkylthio group, a protected or unprotected hydroxyl or amino group, or a nitro group; and A represents CH or C-Y in which Y represents a halogen atom, a substituted or unsubstituted lower alkyl, lower alkoxy or lower alkylthio group, or a protected or unprotected hydroxyl group.

3. The quinolonecarboxylic acid derivative or its salt according to claim 1, wherein $R^2$ represents a substituted or unsubstituted cycloalkyl group.

4. The quinolonecarboxylic acid derivative or its salt according to claim 1, wherein $R^3$ is selected from the group consisting of a hydrogen atom, a halogen atom, a substituted or unsubstituted lower alkyl, lower alkoxy or lower alkylthio group, a nitro group, a cyano group and a protected or unprotected hydroxyl or amino group.

5. The quinolonecarboxylic acid derivative or its salt according to claim 1, wherein $R^3$ is selected from the group consisting of a hydrogen atom, a halogen atom, a substituted or unsubstituted lower alkyl or lower alkoxy group, and a protected or unprotected hydroxyl or amino group.

6. The quinolonecarboxylic acid derivative or its salt according to claim 1, wherein $R^3$ is selected from the group consisting of a hydrogen atom, a halogen atom, a substituted or unsubstituted lower alkyl group, and a protected or unprotected hydroxyl or amino group.

7. The quinolonecarboxylic acid derivative or its salt according to claim 1, wherein $R^4$ is selected from the group consisting of a hydrogen atom, a substituted or unsubstituted lower alkyl group, a lower alkylidene group and a group forming a cycloalkane ring together with the carbon atom to which $R^4$ is bonded.

8. The quinolonecarboxylic acid derivative or its salt according to claim 1, wherein $R^4$ represents a hydrogen atom or a substituted or unsubstituted lower alkyl group.

9. The quinolonecarboxylic acid derivative or its salt according to claim 1, wherein $R^5$ represents a hydrogen atom or a substituted or unsubstituted lower alkyl or cycloalkyl group.

10. The quinolonecarboxylic acid derivative or its salt according to claim 1, wherein $R^5$ represents a hydrogen atom.

11. The quinolonecarboxylic acid derivative or its salt according to claim 1, wherein $R^6$ represents a hydrogen atom, a substituted or unsubstituted lower alkyl group, or a protected or unprotected amino group.

12. The quinolonecarboxylic acid derivative or its salt according to claim 1, wherein $R^6$ represents a hydrogen atom.

13. The quinolonecarboxylic acid derivative or its salt according to claim 1, wherein A represents C-Y in which Y represents a halogen atom, a substituted or unsubstituted alkyl, alkoxy or alkylthio group, or a protected or unprotected hydroxyl group.

14. The quinolonecarboxylic acid derivative or its salt according to claim 1, wherein A represents C-Y in which Y represents a halogen atom, a lower alkyl or lower alkoxy group which may be substituted by one or more halogen atoms, or a protected or unprotected hydroxyl group.

15. 1-Cyclopropyl-7-(isoindolin-5-yl)-8-methoxy-1,4-dihydro-4-oxoquinoline-3-carboxylic acid or its salt.

16. 1-Cyclopropyl-8-difluoromethoxy-7-(isoindolin-5-yl)-1,4-dihydro-4-oxoquinoline-3-carboxylic acid or its salt.

17. 1-Cyclopropyl-8-methoxy-7-(1-methylisoindolin-5-yl)-1,4-dihydro-4-oxoquinoline-3-carboxylic acid, a salt of said acid, an optically active isomer of said acid, or a salt of said isomer.

18. 1-Cyclopropyl-8-difluoromethoxy-7-(1-methylisoindolin-5-yl)-1,4-dihydro-4-oxoquinoline-3-carboxylic acid, a salt of said acid, an optically active isomer of said acid, or a salt of said isomer.

19. An organoboron compound represented by the formula:

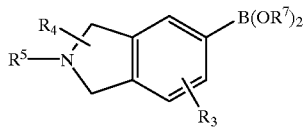

wherein, $R^3$ is selected from the group consisting of a hydrogen atom, halogen atom, a substituted or unsubstituted alkyl, alkenyl, cycloalkyl, aryl, alkoxy or alkylthio group, a nitro group, a cyano group, an acyl group, a protected or unprotected hydroxyl group, and a protected or unprotected, or substituted or unsubstituted amino group; $R^4$ is selected from the group consisting of a hydrogen atom, a halogen atom, a substituted or unsubstituted alkyl, alkenyl, cycloalkyl, aralkyl, aryl alkoxy or alkylthio group, a protected or unprotected hydroxyl or imino group, a protected or unprotected or substituted or unsubstituted amino group, an alkylidene group an oxo group and a group forming a cycloalkane ring together with the carbon atom to which $R^4$ is bonded; $R^5$ represents a hydrogen atom or a substituted or unsubstituted alkyl, cycloalkyl, alkylsulfonyl, arylsulfonyl, acyl or aryl group and $R^7$ represents a hydrogen atom or an alkyl group, or its salt.

20. A pharmaceutical composition comprising a pharmaceutically effective amount of a quinolone derivative or a salt thereof as claimed in claim 1 and a pharmaceutically acceptable preparation adjuvant.

21. A method of treating a bacterial infection, comprising administering the quinolone derivative or salt thereof of claim 1 in an amount effective to provide antibacterial activity.

* * * * *